US007799821B2

(12) United States Patent
Donde et al.

(10) Patent No.: US 7,799,821 B2

(45) Date of Patent: *Sep. 21, 2010

(54) THERAPEUTIC COMPOUNDS

(75) Inventors: Yariv Donde, Dana Point, CA (US); Robert M. Burk, Laguna Beach, CA (US); David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 11/420,885

(22) Filed: May 30, 2006

(65) Prior Publication Data

US 2006/0205800 A1 Sep. 14, 2006

Related U.S. Application Data

(63) Continuation-in-part of application No. 11/009,298, filed on Dec. 10, 2004, now Pat. No. 7,091,231.

(51) Int. Cl.
*A61K 31/4015* (2006.01)
*C07D 409/12* (2006.01)

(52) U.S. Cl. ...................................... 514/422; 548/527

(58) Field of Classification Search ................. 514/422; 548/527

See application file for complete search history.

(56) References Cited

U.S. PATENT DOCUMENTS

| | | | | |
|---|---|---|---|---|
| 4,166,452 | A | 9/1979 | Generales, Jr. | |
| 4,256,108 | A | 3/1981 | Theeuwes | |
| 4,265,874 | A | 5/1981 | Bonsen et al. | |
| 5,462,968 | A | 10/1995 | Woodward | |
| 5,698,598 | A | 12/1997 | Woodward | |
| 5,902,726 | A | 5/1999 | Kliewer et al. | |
| 6,090,847 | A | 7/2000 | Woodward | |
| 6,437,146 | B1 | 8/2002 | Hattori et al. | |
| 6,710,072 | B2 | 3/2004 | Burk et al. | |
| 6,747,037 | B1 | 6/2004 | Old et al. | |
| 7,550,502 | B2 * | 6/2009 | Old et al. | 514/422 |
| 2007/0203222 | A1 * | 8/2007 | Old et al. | 514/422 |
| 2007/0219265 | A1 * | 9/2007 | Old et al. | 514/422 |

FOREIGN PATENT DOCUMENTS

| | | | | |
|---|---|---|---|---|
| WO | 2005/061449 | A1 | | 7/2005 |
| WO | WO 2006/098918 | A2 | * | 9/2006 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*

Francis A. Carey, Organic Chemistry, New York: McGraw-Hill Book Company 1987, p. 63.

Remington's Pharmaceutical Sciences, Mack Publishing Company, Easton, Pa., 16th Edition, 1980.

Dragoli et al, "Parallel Synthesis of Prostaglandin E1 Analogues", J. Comb. Chem. 1999, pp. 534-539.

Baxter, et al., *Synthesis and Use of 7-Substituted Norbornadienes for the Preparation of Prostaglandins and Prostanoids*, J. Chem Soc. Perkins Trans., 1986, p. 889.

Dragoli, et al., *Parallel Synthesis of Prostaglandfin $E_1$* Analogues, J. Comb. Chem. 1999, 534-539, 1980.

* cited by examiner

*Primary Examiner*—Kamal A Saeed
*Assistant Examiner*—Kristin Bianchi
(74) *Attorney, Agent, or Firm*—Kevin J. Forrestal; John E. Wurst; Doina G. Ene

(57) ABSTRACT

A compound having a substituted five or six-membered carbocycle or heterocycle directly bonded to a substituted aryl or heteroaryl ring, wherein said compound has an $EC_{50}$ value of 20 nM or less at the prostaglandin $EP_2$ receptor according to the cAMP assay.

Methods, compositions, and medicaments related thereto are also disclosed.

19 Claims, No Drawings

THERAPEUTIC COMPOUNDS

CROSS-REFERENCE TO RELATED APPLICATIONS

This application is a continuation-in-part of U.S. patent application Ser. No. 11/009,298, filed on Dec. 10, 2004 now U.S. Pat. No. 7,091,231, the disclosure of which is expressly incorporated by reference herein.

DESCRIPTION OF THE INVENTION

A compound having a substituted five or six-membered carbocycle or heterocycle directly bonded to a substituted aryl or heteroaryl ring, wherein said compound has an $EC_{50}$ value of 20 nM or less in HEK-EBNA cells expressing a PG EP2 receptor subtype according to the cAMP assay is disclosed herein.

In one embodiment, the compound reduces intraocular pressure of a beagle dog by at least 4 mmHg when administered topically in a liquid composition to an eye of said dog, wherein compound has a concentration of about 0.3% (w/v) or less in said composition.

Intraocular pressure studies in dogs involved pneumatonometry performed in conscious, Beagle dogs of both sexes (10-15 kg). The animals remained conscious throughout the study and were gently restrained by hand. Drugs were administered topically to one eye as a 25 μL volume drop, the other eye received 25 μL vehicle (0.1% (w/v) polysorbate 80; 10 mM TRIS) as a control. Proparacaine (0.1% w/v) was used for corneal anesthesia during tonometry. Intraocular pressure was determined just before drug administration and at 2, 4 and 6 hr thereafter on each day of the 5 day study. Drug was administered immediately after the first IOP reading.

In another embodiment, the compound reduces intraocular pressure of a human with glaucoma or elevated intraocular pressure by at least 5 mmHg when administered topically in a liquid composition to an eye of said human, wherein compound has a concentration of about 0.3% (w/v) or less in said composition.

"The cAMP assay" is:

A 384-well drug plate was prepared to contain 6 test compounds, PGE2 and cAMP in 16 serial dilutions in triplicate, using a Biomek station. HEK-EBNA cells expressing a target PG receptor subtype (EP2 or EP4) were suspended in a stimulation buffer (HBSS, 0.1% BSA, 0.5 mM IBMX and 5 mM HEPES, pH 7.4) in a density of $10^4$ cells/5 μl. The reaction was initiated by mixing 5 μL drug dilutions with 5 μl of HEK-EBNA cells in a well, carried out for 30 min at room temperature, and followed by the addition of 5 μl anti-cAMP acceptor beads in the control buffer with Tween-20 (25 mM NaCl, 0.03% Tween-20, 5 mM HEPES, pH7.4). After 30 min in the dark at room temperature, the mixtures were incubated with 15 μl biotinylated-cAMP/strepavidin donor beads in Lysis/Detection buffer (0.1% BSA, 0.3% Tween-20 and 5 mM HEPES, pH7.4) for 45 min at the room temperature. Fluorescence changes were read using a Fusion-alpha HT microplate reader.

Reduction of intraocular pressure of a beagle dog by at least 4 mmHg is determined by the procedure described herein.

Reduction of intraocular pressure in a human with glaucoma or elevated intraocular pressure by at least 5 mmHg is done on a person whose intraocular pressure is elevated more than 5 mmHg above normal.

Another embodiment is a compound of the formula

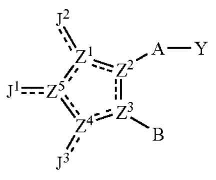

or

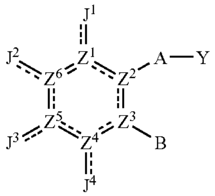

or a pharmaceutically acceptable salt thereof, or a prodrug thereof, or a tautomer thereof;

wherein a dashed line represents the presence or absence of a bond, provided that an atom does not have a double bond to two different ligands;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;

$Z^1$, $Z^2$, $Z^3$, $Z^4$, $Z^5$, and $Z^6$ are independently $CH_2$, CH, C, NH, or N; provided that at least one of $Z^1$, $Z^2$, $Z^3$, $Z^4$, $Z^5$, and $Z^6$ is not NH or N;

$J^1$, $J^2$, $J^3$, $J^4$ are independently hydrogen; F; Cl, Br; I; O; OH; S; SH; O-alkyl having 1, 2, 3, 4, 5 or 6 carbon atoms; alkyl having 1, 2, 3, 4, 5, or 6 carbon atoms; or $CF_3$; and B is substituted aryl or substituted heteroaryl.

Another embodiment is a compound comprising

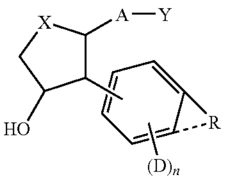

or a pharmaceutically acceptable salt or a prodrug thereof, wherein a dashed line represents the presence or absence of a covalent bond;

Y is a carboxylic acid, sulfonic acid, or phosphonic acid; or an amide or ester thereof comprising from 0 to 12 carbon atoms; or Y is a hydroxymethyl, or tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is substituted or unsubstituted phenyl or monocyclic heteroaryl, the sum of m and o is from 1 to 4, and wherein one $CH_2$ may be substituted with S or O;

X is C=O, CHF, $CF_2$, CHCl, or CHOH; wherein if X is CHOH, then OH is in the β-configuration;

R is a hydrocarbyl or a hydroxyhydrocarbyl moiety comprising from 1 to 12 carbon atoms;

D is independently a moiety comprising from 1 to 6 non-hydrogen atoms; and n is an integer from 0 to 4.

A compound comprising a prostaglandin $EP_2$ selective agonist wherein the ω-chain comprises a substituted phenyl, wherein at least one substituent consists of hydrocarbyl or non-linear hydroxyhydrocarbyl, is also disclosed herein.

Several of the carbon atoms on these compounds are chiral centers. While not intending to limit the scope of the invention in any way, or be bound in any way by theory, it is believed that many compounds and pharmaceutically active salts or prodrugs thereof having the stereochemistry shown below are particularly useful.

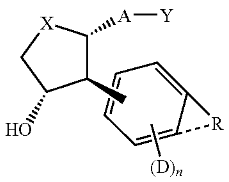

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

However, it is also advantageous if one or more of the bonds has the indicated stereochemistry, while the stereochemistry of other bonds to chiral centers may vary. Thus, while not intending to limit the scope of the invention in any way, compounds comprising

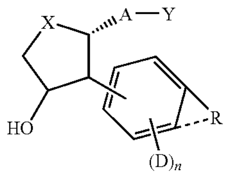
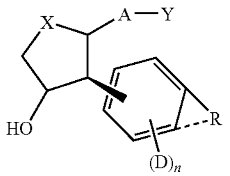
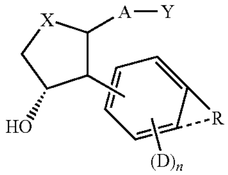
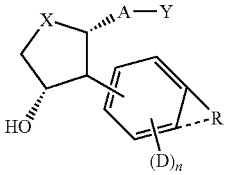
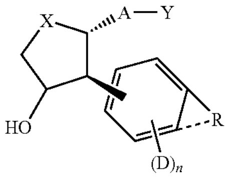
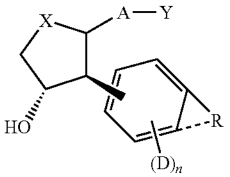

and the like, and pharmaceutically acceptable salts and prodrugs thereof, are particularly useful in the context disclosed herein.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Y is a carboxylic acid, sulfonic acid, or phosphonic acid functional group; or an amide or ester thereof comprising from 0 to 12 carbon atoms; or Y is a hydroxymethyl, or tetrazolyl functional group. Thus, while not intending to limit the scope of the invention in any way, in certain compounds Y is a carboxylic acid, sulfonic acid, or phosphonic acid functional group, i.e. one of the structures shown below.

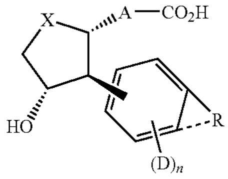
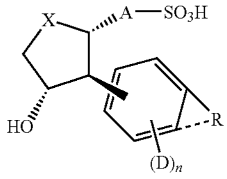
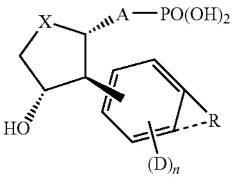

Salts of any of these acids of any pharmaceutically acceptable form may also be present.

Additionally, an amide or ester of one of the organic acids shown above comprising from 0 to 12 carbon atoms is also contemplated. In an ester, a hydrocarbyl moiety replaces a hydrogen of an acid such as in a carboxylic acid ester, e.g. $CO_2R^3$. In an amide, an amine group replaces an OH of the acid. An amine is a moiety having a central nitrogen which has exactly three bonds to C or H. Examples of amides include $CON(R^3)_2$, $CON(OR^3)R^3$, $CON(CH_2CH_2OH)_2$, and $CONH(CH_2CH_2OH)$. Moieties such as $CONHSO_2R^3$ are also amides of the carboxylic acid notwithstanding the fact that they may also be considered to be amides of the sulfonic acid $R^3$—$SO_3H$.

Finally, while not intending to limit the scope of the invention in any way, Y may also be a hydroxymethyl, or a tetrazolyl functional group, i.e. compounds having a structure such as one of those shown below.

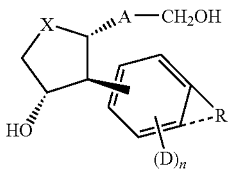

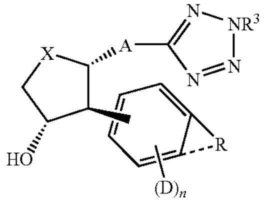

When $R^3$ is hydrogen, the tetrazolyl functional group has two tautomeric forms, which can rapidly interconvert in aqueous or biological media, and are thus equivalent to one another. These tautomers are shown below.

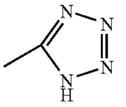

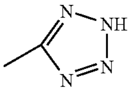

Additionally, if $R^3$ is $C_1$-$C_6$ alkyl, phenyl, or biphenyl, other isomeric forms of the tetrazolyl functional group such as the one shown below are also possible, all of these are considered to be within the scope of the term "tetrazolyl."

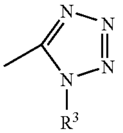

While not intending to limit the scope of the invention in any way, in one embodiment, Y is selected from the group consisting of $CO_2(R^3)$, $CON(R^3)_2$, $CON(OR^3)R^3$, $CON(CH_2CH_2OH)_2$, $CONH(CH_2CH_2OH)$, $CH_2OH$, $P(O)(OH)_2$, $CONHSO_2R^3$, $SO_2N(R^3)_2$, $SO_2NHR^3$, and tetrazolyl-$R^3$; wherein $R^3$ is independently H, $C_1$-$C_6$ alkyl, phenyl, or biphenyl.

In relation to the identity of A disclosed in the chemical structures presented herein, in the broadest sense, A is $-(CH_2)_6-$, cis $-CH_2CH{=}CH-(CH_2)_3-$, or $-CH_2C{\equiv}C-(CH_2)_3-$, wherein 1 or 2 carbon atoms may be substituted with S or O; or A is $-(CH_2)_m-Ar-(CH_2)_o-$ wherein Ar is substituted or unsubstituted phenyl or monocyclic heteroaryl, the sum of m and o is from 1 to 3, and wherein one $CH_2$ may be substituted with S or O.

In other words, while not intending to be limiting, A may be $-(CH_2)_6-$, cis $-CH_2CH{=}CH-(CH_2)_3-$, or $-CH_2C{\equiv}C-(CH_2)_3-$.

Alternatively, A may be a group which is related to one of these three moieties in that any carbon is substituted with S or O. For example, while not intending to limit the scope of the invention in any way, A may be an S substituted moiety such as one of the following or the like.

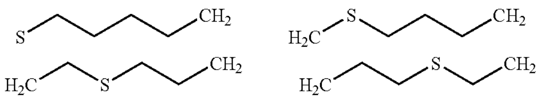

-continued

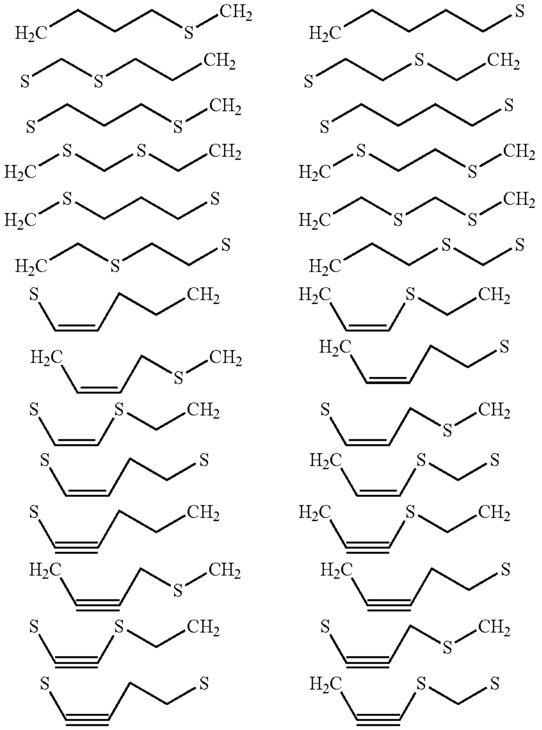

Alternatively, while not intending to limit the scope of the invention in any way, A may be an O substituted moiety such as one of the following or the like.

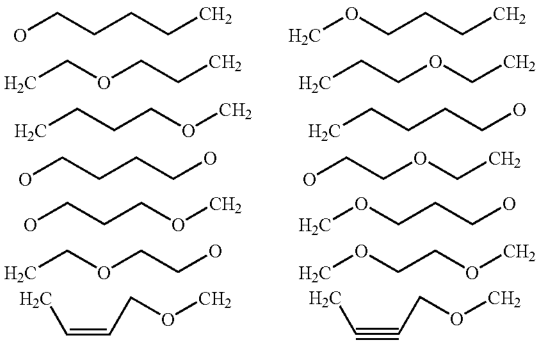

Alternatively, while not intending to limit the scope of the invention in any way, A may have both an O and an S substituted in the chain, such as one of the following or the like.

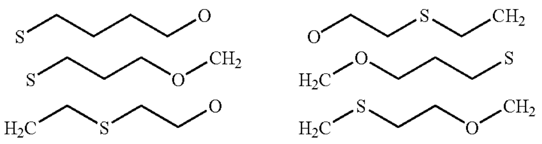

Alternatively, while not intending to limit the scope of the invention in any way, in certain embodiments A is $-(CH_2)_m-Ar-(CH_2)_o-$ wherein Ar is substituted or unsubstituted phenyl or monocyclic heteroaryl, the sum of m and o is from 1 to 4, and wherein one $CH_2$ may be substituted with S or O. In other words, while not intending to limit the scope of the invention in any way, A comprises from 1 to 4 $CH_2$ moieties and Ar, e.g. $-CH_2-Ar-$, $-(CH_2)_2-Ar-$, $-CH_2-ArCH_2-$, $-CH_2Ar(CH_2)_2-$, $-(CH_2)_2-Ar(CH_2)_2-$, and the like; or A comprises O, from 0 to 3 $CH_2$ moieties, and Ar, as in for example, $-O-Ar-$, $Ar-CH_2-O-$, $-O-Ar-(CH_2)_2-$, $-O-CH_2-Ar-$, $-O-CH_2-Ar-(CH_2)_2$, and the like; or A comprises S, from 0 to 3 $CH_2$ moieties, and Ar, as in for example, $-S-Ar-$, $Ar-CH_2-S-$, $-S-Ar-(CH_2)_2-$, $-S-CH_2-Ar-$, $-S-CH_2-Ar-(CH_2)_2$, and the like.

Ar is substituted or unsubstituted phenyl or substituted or unsubstituted monocyclic heteroaryl. In one embodiment, Ar is substituted or unsubstituted phenyl, thienyl, furyl, or pyridinyl. In another embodiment Ar is phenyl (Ph). In another embodiment A is $-(CH_2)_2-Ph$. While not intending to limit scope of the invention in any way, substituents may have 4 or less heavy atoms, or in other words, non hydrogen atoms. Any number of hydrogen atoms required for a particular substituent will also be included. Thus, the substituent may be C4 or lower hydrocarbyl, including C4 or lower alkyl, alkenyl, alkynyl, and the like; C3 or lower hydrocarbyloxy; $CF_3$; halo, such as F, Cl, or Br; hydroxyl; $NH_2$ and alkylamine functional groups up to C3; other N or S containing substituents; and the like.

In one embodiment A is $-(CH_2)_m-Ar-(CH_2)_o-$ wherein Ar is phenyl, the sum of m and o is from 1 to 3, and wherein one $CH_2$ may be substituted with S or O.

In another embodiment A is $-CH_2-Ar-OCH_2-$. In another embodiment A is $-CH_2-Ar-OCH_2-$ and Ar is phenyl.

In another embodiment A is $-(CH_2)_6-$, cis $-CH_2CH{=}CH-(CH_2)_3-$, or $-CH_2C{\equiv}C-(CH_2)_3-$, wherein 1 or 2 carbon atoms may be substituted with S or O; or A is $-(CH_2)_2-Ph-$ wherein one $CH_2$ may be substituted with S or O.

In another embodiment A is $-(CH_2)_6-$, cis $-CH_2CH{=}CH-(CH_2)_3-$, or $-CH_2C{\equiv}C-(CH_2)_3-$, wherein 1 or 2 carbon atoms may be substituted with S or O; or A is $-(CH_2)_2-Ph-$.

D is a moiety comprising from 1 to 6 non-hydrogen atoms, in other words, there are from 1 to 6 atoms which are not hydrogen, and any number of hydrogen atoms required to form the complete substituent. For example, a methyl substituent has 1 carbon atom and 3 hydrogen atoms. Other example substituents include other hydrocarbyl moieties comprising from 1 to 6 carbon atoms including alkyl such as ethyl, propyl, isopropyl, butyl and isomers thereof, pentyl and isomers thereof, hexyl and isomers thereof, cyclic and unsaturated hydrocarbyls having 1 to 6 carbon atoms; $CO_2H$ and salts thereof, alkoxy up to $C_5$ such as methoxy, ethoxy, propoxy, isopropoxy, a butoxy isomer, or a pentoxy isomer; carboxylic acid esters; CN; $NO_2$; $CF_3$; F; Cl; Br; I; sulfonyl esters; $SO_3H$ and salts thereof, and the like. D may be in any reasonable position on the phenyl ring.

In certain compounds, n is 0. In other compounds n is 1, in other compounds n is 2, and in other compounds n is 3.

A hydrocarbyl moiety refers to a moiety consisting of only carbon and hydrogen. While not intending to limit the scope of the invention in any way, examples of different types of hydrocarbyl moiety are as follows.

On type of hydrocarbyl is alkyl including:

a) linear alkyl such as methyl, ethyl, propyl, n-butyl, n-pentyl, n-hexyl, and the like;
b) branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;
c) cycloalkyl such as cyclopropyl, cyclobutyl, cyclopentyl, cyclohexyl, cycloheptyl, etc.; and
d) alkyl fragments consisting of both cyclic and noncyclic components, whether linear or branched, which may be attached to the remainder of the molecule at any available position including terminal, internal, or ring carbon atoms.

In analogy to alkyl, there is linear, branched, cycloalkyl, and combination hydrocarbyl.

Another type of hydrocarbyl is alkenyl, which is similar to alkyl with the exception that a double bond is present.

Another type of hydrocarbyl is alk(poly)enyl, which is similar to alkenyl, except that more than one double bond is present.

Another type of hydrocarbyl is alkynyl or an alk(poly)ynyl, which is similar to alkenyl or alk(poly)ynyl except that one or more triple bonds are present.

Another type of hydrocarbyl is aryl, which includes phenyl, naphthyl and other aromatic hydrocarbyls.

Additionally, combinations of any of the above in any manner imaginable to those of ordinary skill in the art are also hydrocarbyl.

A hydrocarbyl moiety comprising a cyclic structure comprises a cycloalkyl, cycloalkenyl, cycloalkynyl, cycloalkyl (poly)enyl, cycloalkyl(poly)ynyl, aryl, and the like; and may consist of only the ring or may be a combination of the ring and one or more of the linear, branched, or cyclic hydrocarbyl fragments; or may be a fused polycyclic structure.

A hydroxyhydrocarbyl moiety consists of a combination of a hydrocarbyl moiety and a hydroxyl group. In other words, a hydrogen atom of the hydrocarbyl moiety is substituted with a hydroxyl group. The hydroxyhydrocarbyl moiety attaches to the remainder of the molecule at a carbon atom.

Thus, while not intending to limit the scope of the invention in any way, as R is a hydrocarbyl or a hydroxyhydrocarbyl moiety comprising from 1 to 12 atoms, embodiments having R as any of the hydrocarbyl or hydroxycarbyl moieties listed above are specifically contemplated herein. R may also be a different moiety which may be considered hydrocarbyl or hydroxyhydrocarbyl according to the description given herein.

In certain compounds, R is a hydroxyhydrocarbyl having the hydroxyl group attached to the carbon atom which is also attached to the remainder of the molecule. In other words the hydroxyl group and the remainder of the molecule are on geminal positions on the hydrocarbyl moiety. This type of hydroxyhydrocarbyl moiety is referred to as a 1-hydroxyhydrocarbyl moiety herein. Non-linear hydroxyhydrocarbyl is hydroxyhydrocarbyl wherein the hydrocarbyl portion is not linear, i.e. it has branching and/or a ring.

In other compounds R is hydroxyhydrocarbyl having the hydroxyl group attached to a carbon atom which is directly attached to the remaining part of the molecule. These particular hydroxyhydrocarbyl are called 2-hydroxyhydrocarbyl herein. For example, $-C(CH_3)_2CH_2OH$ is 2-hydroxyhydrocarbyl. While not intending to limit the scope of the invention in any way, a general structure where R is 2-hydrocarbyl is shown below.

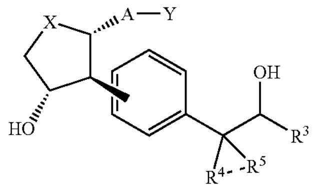

As with all other structures shown herein, pharmaceutically acceptable salts and prodrugs of compounds represent by these structures are also contemplated.

In one embodiment related to the above structure, $R^3$, $R^4$, and $R^5$ are independently H or $C_{1-6}$ alkyl. As the dashed line indicates the presence or absence of a bond, $R^4$ and $R^5$ may be two separate moieties. For example, while not intending to be limiting, $R^4$ and $R^5$ may be methyl, and no bond would be present where indicated by the dashed line. Alternatively, while not intending to limit the scope of the invention in any way, $R^4$ and $R^5$ may form a ring. In other words, a compound such as the one shown below is possible, wherein x is from 1 to 6.

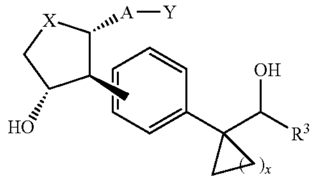

Pharmaceutically acceptable salts and prodrugs of compounds represent by these structures are also contemplated.

In certain compounds, R comprises from 6 to 9 carbon atoms and a cyclic structure. In other compounds, R comprises from 1 to 5 carbon atoms. In certain compounds R is hydroxyalkyl having from 1 to 5 carbon atoms. In other compounds R is a 1-hydroxyhydrocarbyl moiety comprising from 6 to 9 carbon atoms and a cyclic structure. In other compounds R is a 1-hydroxyhydrocarbyl moiety comprising from 6 to 9 carbon atoms and a cyclic structure comprising from 4-7 carbon atoms. In other words, the cyclic structure part of R is a cyclobutyl, cyclopentyl, cyclohexyl, or cycloheptyl fragment. The cyclic structure part of R may also be a cycloalkenyl or cycloalkynyl fragment such as cyclopentene or cyclohexene. In other compounds R is a hydrocarbyl moiety comprising from 1 to 5 carbon atoms. In other words, R is methyl, ethyl, propyl, isopropyl, a butyl isomer such as t-butyl, or a pentyl isomer. In certain compounds R is t-butyl.

Certain R groups are specifically contemplated herein. These are shown below, where PR represents the remaining part of the molecule.

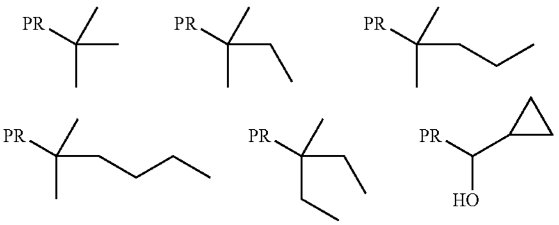

-continued

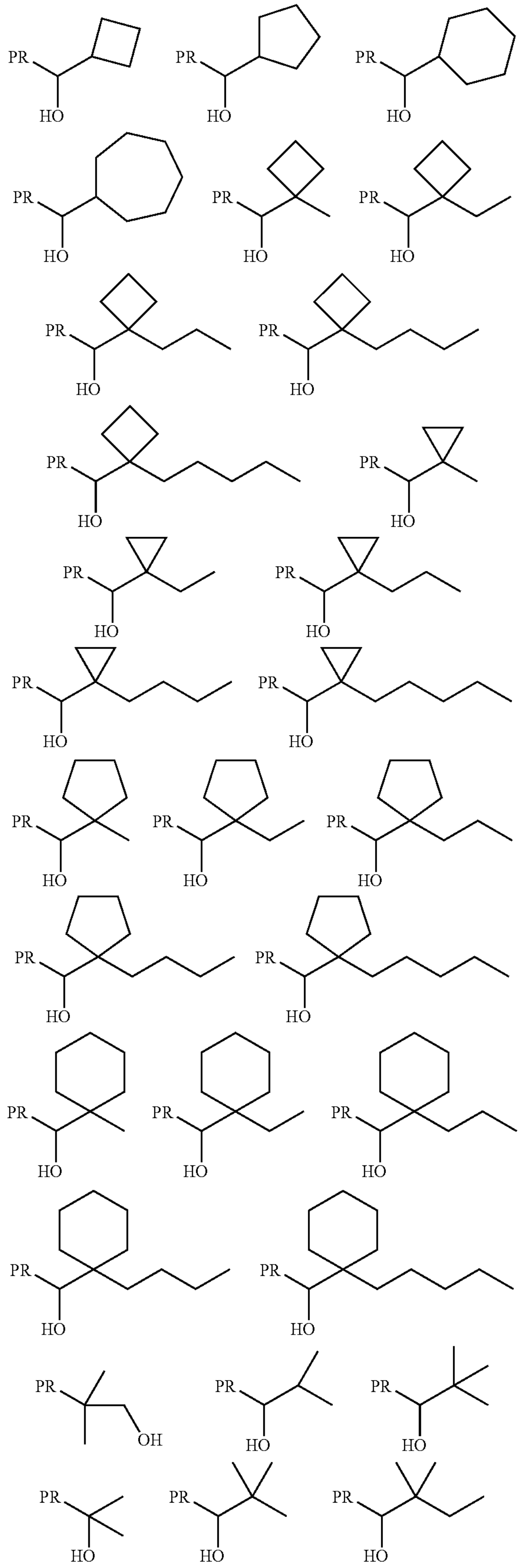

-continued

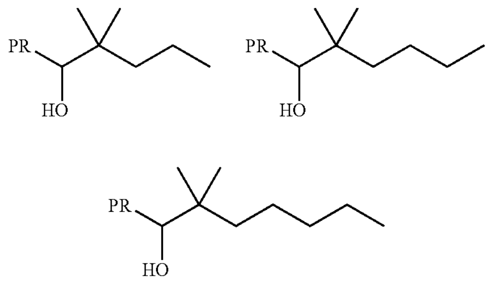

As there is a dashed line between R and the phenyl ring, cyclic structures having two carbon atoms of the phenyl ring are possible. While not intending to limit the scope of the invention in any way, compounds such as those represented by the structure below are therefore possible.

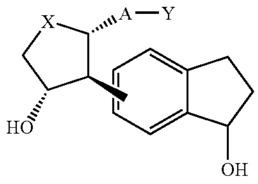

Pharmaceutically acceptable salts and prodrugs thereof are also contemplated.

Other useful compounds comprise

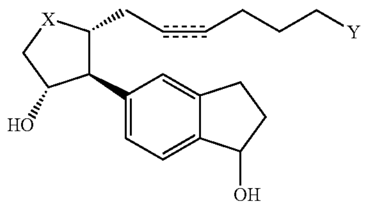

or a pharmaceutically acceptable salt, or a prodrug thereof.

Other useful compounds comprise

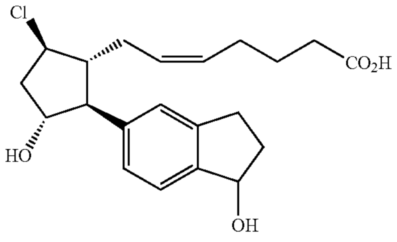

or a pharmaceutically acceptable salt, or a prodrug thereof.

Those of ordinary skill in the art understand that any value which refers to the number of atoms, moieties, etc., on a small molecule will be an integer, i.e. 0, 1, 2, 3, etc.

Certain useful compounds comprise

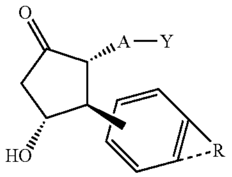

or a pharmaceutically acceptable salt, or a prodrug thereof.

Other useful compounds comprise

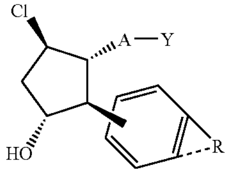

or a pharmaceutically acceptable salt, or a prodrug thereof.

Other useful examples of compounds comprise

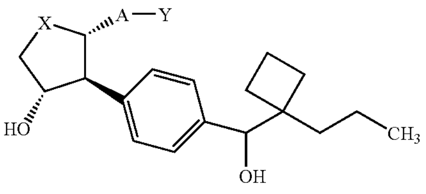

or a pharmaceutically acceptable salt, or a prodrug thereof.

Other compounds comprise

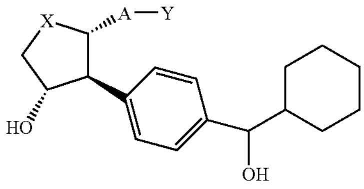

or a pharmaceutically acceptable salt, or a prodrug thereof.

Other embodiments comprise

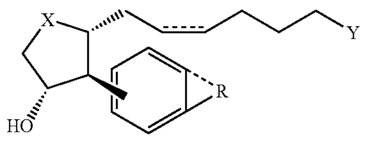

or a pharmaceutically acceptable salt, or a prodrug thereof, wherein a dashed line indicates the presence or absence of a bond.

Other compounds comprise

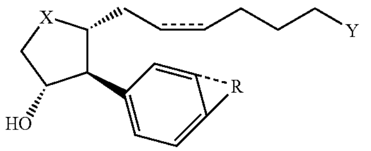

wherein X is C═O or CHCl; and

R is alkyl having from 3 to 6 carbon atoms.

Other compounds comprise

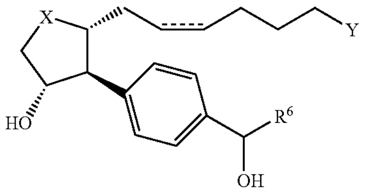

or a pharmaceutically acceptable salt, or a prodrug thereof, wherein $R^6$ is cycloalkyl comprising from 3 to 10 carbon atoms; and X is C═O or CHCl.

Other compounds comprise

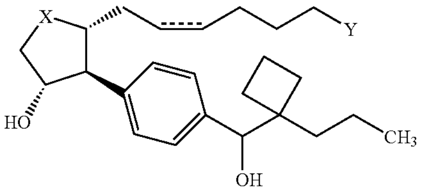

or a pharmaceutically acceptable salt, or a prodrug thereof.

Other embodiments comprise

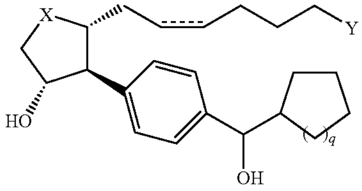

or a pharmaceutically acceptable salt, or a prodrug thereof wherein q is an integer having a value of from 0 to 3.

Other compounds comprise

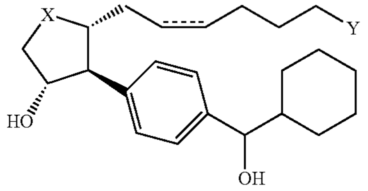

or a pharmaceutically acceptable salt, or a prodrug thereof.

Other compounds comprise

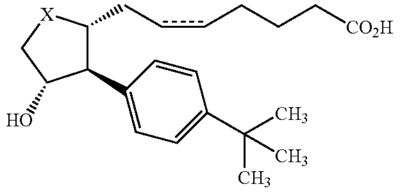

or a pharmaceutically acceptable salt, or a prodrug thereof.

Other useful compounds comprise

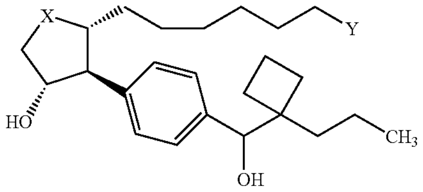

or a pharmaceutically acceptable salt, or a prodrug thereof.

Other useful embodiments comprise

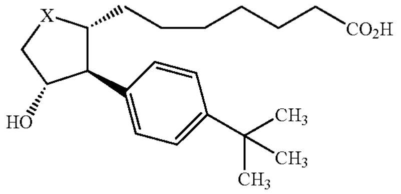

or a pharmaceutically acceptable salt, or a prodrug thereof.

Another useful compound is

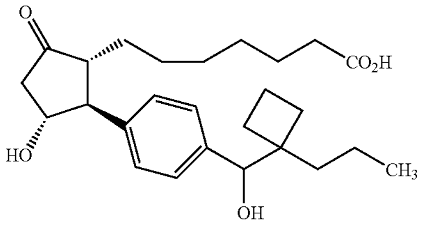

or a pharmaceutically acceptable salt, or a prodrug thereof.

Another useful compound is

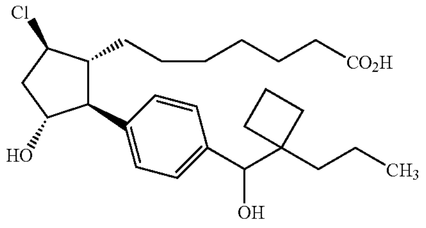

or a pharmaceutically acceptable salt, or a prodrug thereof.

Another useful compound is

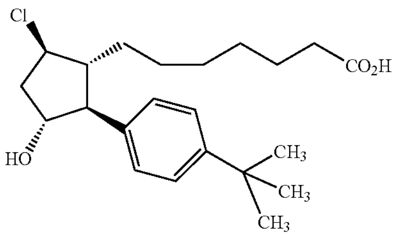

or a pharmaceutically acceptable salt, or a prodrug thereof.

Another useful compound is

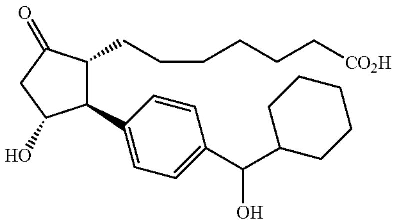

or a pharmaceutically acceptable salt, or a prodrug thereof.

Another useful compound is

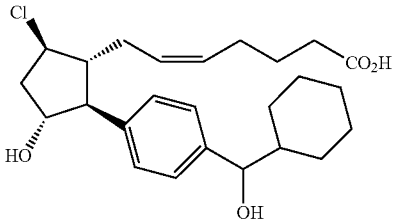

or a pharmaceutically acceptable salt, or a prodrug thereof.

Certain compounds comprise

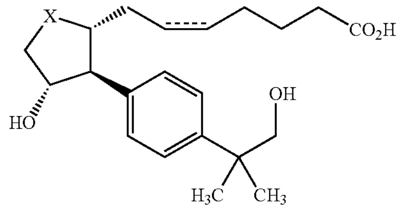

or a pharmaceutically acceptable salt or a prodrug thereof.

Other compounds comprise

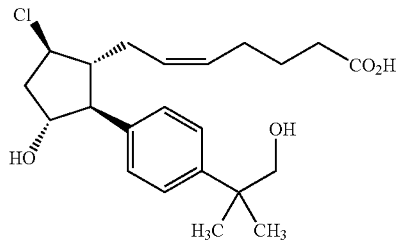

or a pharmaceutically acceptable salt or a prodrug thereof.

Another useful compound is

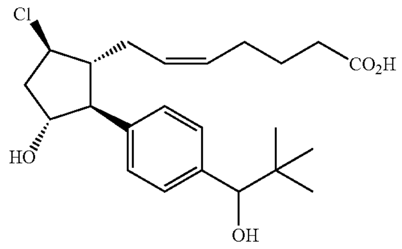

or a pharmaceutically acceptable salt, or a prodrug thereof.

Another useful compound is

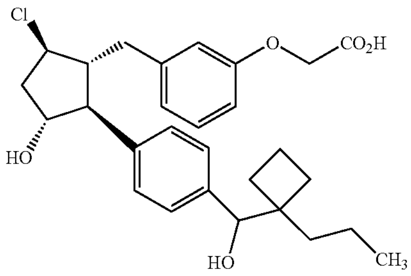

or a pharmaceutically acceptable salt or a prodrug thereof.

Another useful compound is

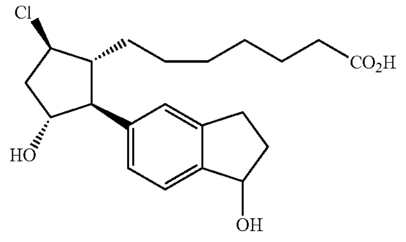

or a pharmaceutically acceptable salt or a prodrug thereof.

Other compounds comprise

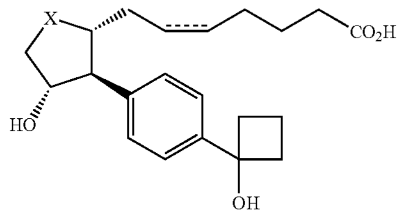

or a pharmaceutically acceptable salt or a prodrug thereof wherein X is C═O or CHCl.

Another useful compound is

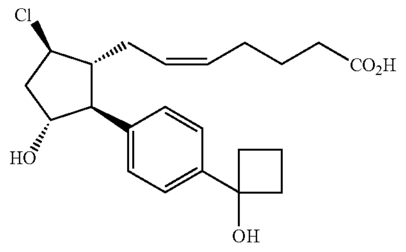

or a pharmaceutically acceptable salt or a prodrug thereof.

A prostaglandin $EP_2$ selective agonist is a compound which is more active at a prostaglandin $EP_2$ receptor than at any other prostaglandin receptor.

In one embodiment, the compound has an $IC_{50}$ value less than 1 μM. In another embodiment, the compound is more than 100 times more active at the $EP_2$ receptor than at any other receptor. In another embodiment, the compound is more than 1000 times more active at the $EP_2$ receptor than at any other receptor.

The ω-chain has the meaning normally understood in the art. In prostaglandin $E_2$, the ω-chain is in the third position of the cyclopentanone ring, where the position 1 is the carbonyl and the α-chain is at position 2. However, the meaning of the term α-chain should be adapted according to synthetic variations that are made to prostaglandin $E_2$. A person of ordinary skill in the art can readily discern the ω-chain in synthetic analogs and derivatives of prostaglandin $E_2$. For example, while not intending to limit the scope of the invention in any way, the ω-chain could be at the third position in a 1-chlorocyclopentane having the α-chain in the 2 position.

A substituted phenyl, wherein at least one substituent consists of hydrocarbyl or non-linear hydroxyhydrocarbyl may have additional substituents which are not hydrocarbyl or non-linear hydroxyhydrocarbyl, i.e. at least one substituent is hydrocarbyl or non-linear hydroxyhydrocarbyl and at least one substituent is not.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A number of exemplary compounds, and exemplary methods of making these compounds, are identified in the following patent applications, all of which are expressly incorporated by reference herein:

U.S. Provisional Patent Application No. 60/678,403, filed on May 6, 2005;

U.S. Provisional Patent Application No. 60/742,779, filed on Dec. 6, 2005;

U.S. Provisional Patent Application No. 60/777,506, filed Feb. 29, 2006;

U.S. Provisional Patent Application No. 60/660,748, filed on Mar. 10, 2005;

U.S. Provisional Patent Application No. 60/783,979; filed on Mar. 20, 2005;

U.S. Provisional Patent Application No. 60/744,236; filed on Apr. 4, 2006;

U.S. Provisional Patent Application No. 60/746,393; filed on May 4, 2006;

U.S. Provisional Patent Application No. 60/746,391; filed on May 4, 2006;

U.S. Provisional Patent Application No. 60/747,835; filed on May 22, 2006;

U.S. Provisional Patent Application No. 60/747,115; filed on May 2, 2006; and

U.S. Provisional Patent Application No. 60/803,040, filed on May 24, 2006.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

EXAMPLE 2

Binding Data

Ki

Competition binding experiments were performed in a medium containing Hank's balanced salt solution, Hepes 20 mM, pH 7.3, membranes (~60 μg protein) or $2\times10^5$ cells from HEK 293 cells stably expressing human EP2 receptors, [$^3$H]PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Recptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17 —phenyl $PGF_{2\alpha}$ (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radioligand for EP receptors. [$^3$H] 17-phenyl $PGF_{2\alpha}$ was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]—$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geqq 3$.

The results of the binding and activity studies, presented in the Tables below, demonstrate that the compounds disclosed herein are selective prostaglandin $EP_2$ agonists, and are thus useful for the treatment of glaucoma, ocular hypertension, the other diseases or conditions disclosed herein.

| | BINDING IC50 (nm) | | | FUNCTIONAL EC50 (nm) | | | | | | | |
|---|---|---|---|---|---|---|---|---|---|---|---|
| STRUCTURE | HEP2 | HEP3 | HEP4 | HFP | HEP1 | HEP2 | HEP3A | HEP4 | HTP | HIP | HDP |
| 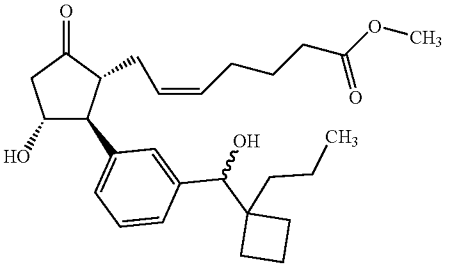 | | | | NA | NA | >10 K | >10 K | >10 K | NA | NA | NA |
| 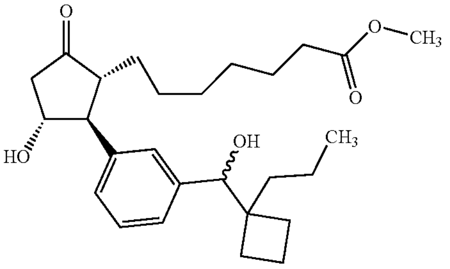 | | | | NA | NA | >10 K | >10 K | >10 K | NA | >10 K | >10 K |

-continued
| | BINDING IC50 (nm) | | | FUNCTIONAL EC50 (nm) | | | | | | | |
|---|---|---|---|---|---|---|---|---|---|---|---|
| STRUCTURE | HEP2 | HEP3 | HEP4 | HFP | HEP1 | HEP2 | HEP3A | HEP4 | HTP | HIP | HDP |
| 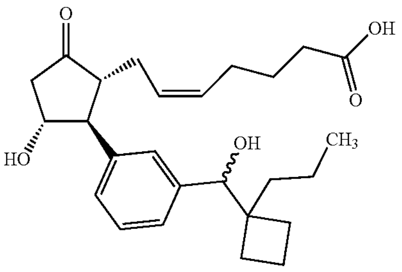 | | | | NA | NA | 5294 | 1698 | NA | NA | NA | NA |
| 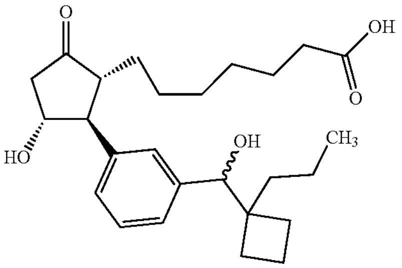 | | | | NA | NA | 5259 | | NA | NA | NA | NA |
| 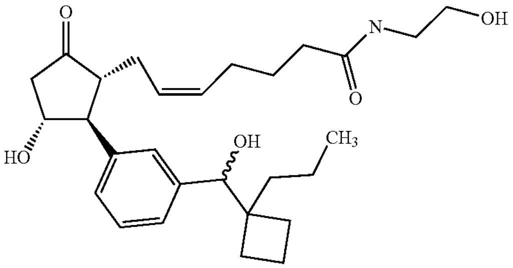 | | | | NA | NA | NA | NA | NA | NA | NA | NA |
| 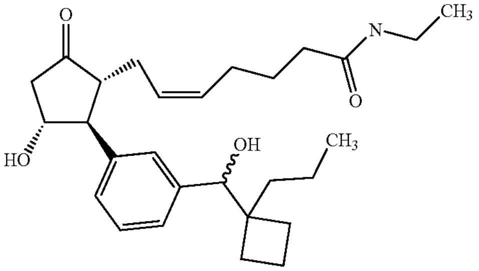 | | | | NA | NA | >10 K | NA | >10 K | NA | NA | NA |
| 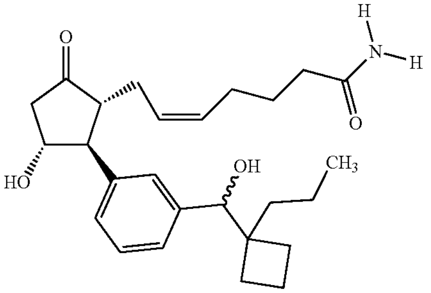 | | | | NA | NA | NA | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 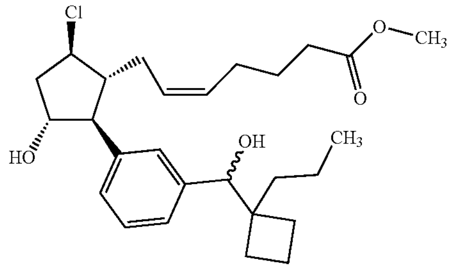 | | | | NA | NA | >10 K | >10 K | NA | >10 K | NA | NA |
| 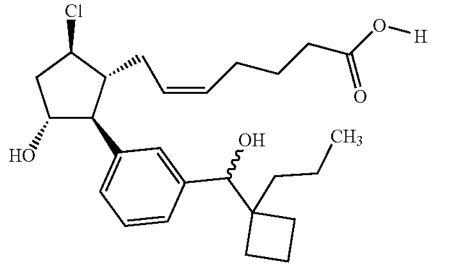 | | | | NA | NA | 322 | 455 | NA | >10 K | NA | >10 K |
| 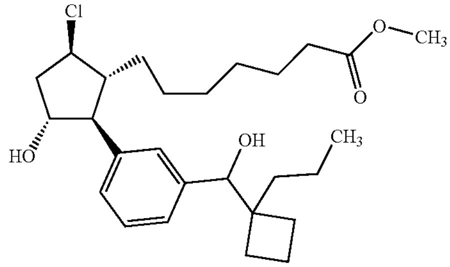 | | | | NA | NA | NA | NA | NA | NA | NA | NA |
| 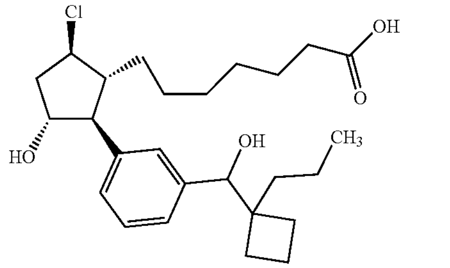 | | | | NA | NA | 1479 | 3118 | NA | NA | NA | NA |
| 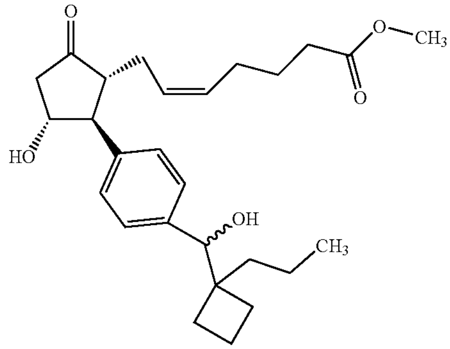 | | | | NA | NA | NA | NA | NA | >10 K | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 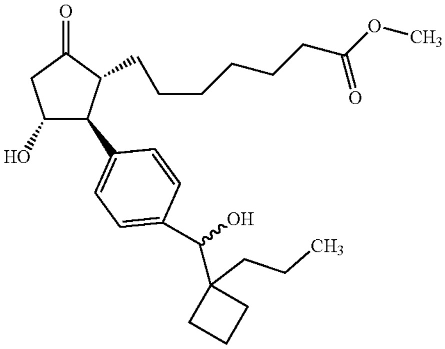 | | | | NA | NA | >10 K | NA | NA | NA | NA | NA |
| 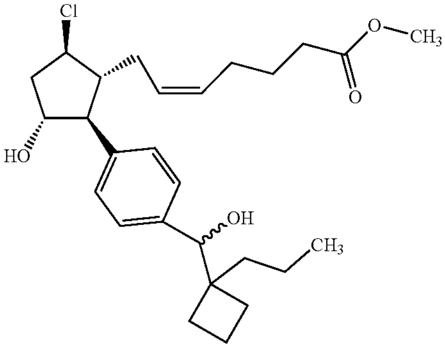 | | | | NA | NA | >10 K | NA | NA | NA | NA | NA |
| 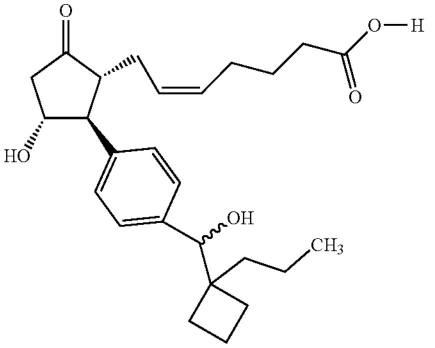 | | | | NA | NA | 3723 | NA | NA | NA | NA | NA |
| 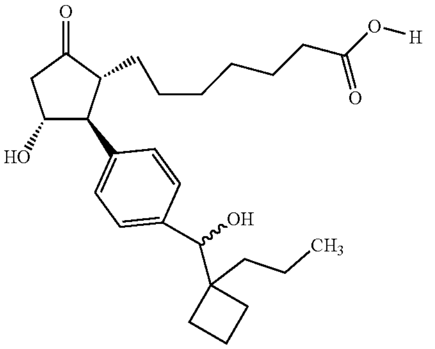 | | | | NA | NA | 635 | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 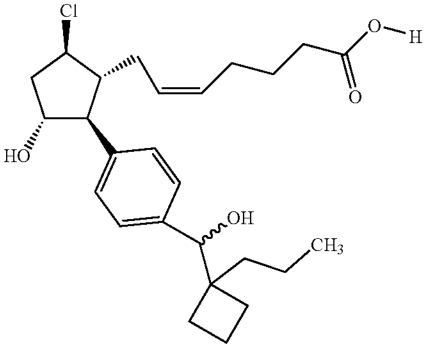 | | | | NA | NA | 2270 | NA | NA | NA | NA | NA |
| 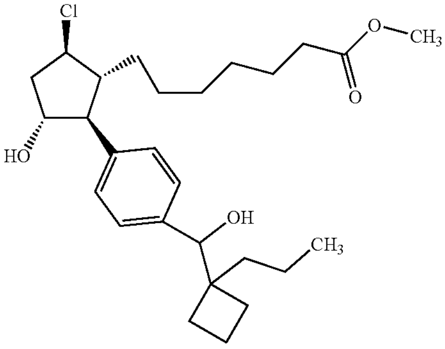 | | | | NA | NA | NA | NA | NA | NA | NA | NA |
| 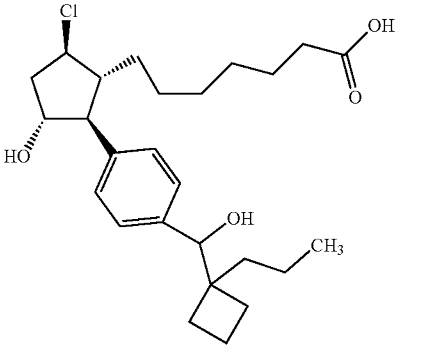 | | | | NA | NA | 546 | NA | NA | NA | NA | NA |
| 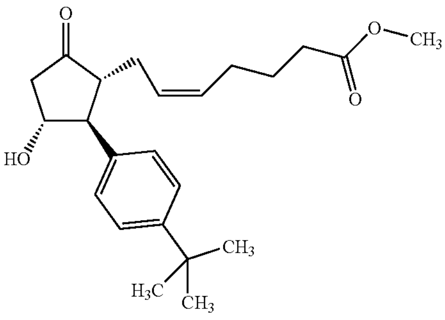 | | | | NA | NA | >10 K | NA | NA | >10 K | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 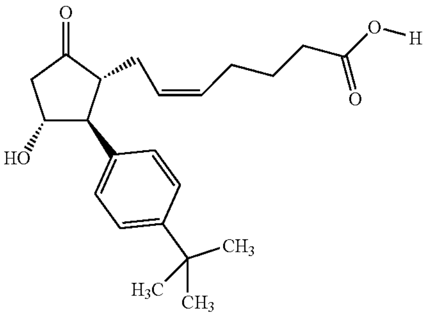 | | | | NA | >10 K | 1709 | NA | NA | NA | NA | NA |
| 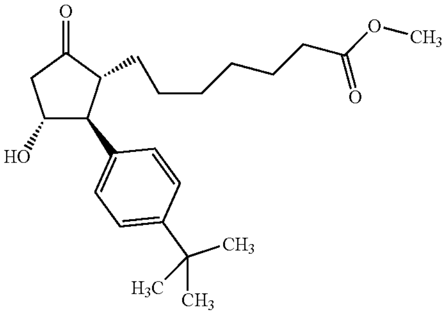 | | | | NA | NA | 936 | >10 K | >10 K | >10 K | NA | NA |
| 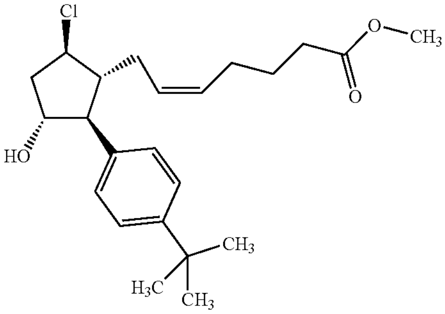 | | | | NA | NA | >10 K | >10 K | NA | NA | NA | NA |
| 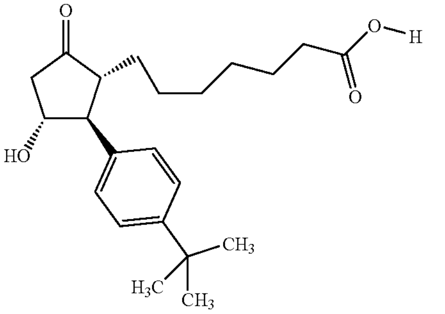 | | | | NA | >10 K | 102 | 3390 | NA | 4273 | >10 K | NA |

-continued
| STRUCTURE | BINDING IC50 (nm) | | | FUNCTIONAL EC50 (nm) | | | | | | | |
|---|---|---|---|---|---|---|---|---|---|---|---|
| | HEP2 | HEP3 | HEP4 | HFP | HEP1 | HEP2 | HEP3A | HEP4 | HTP | HIP | HDP |
| 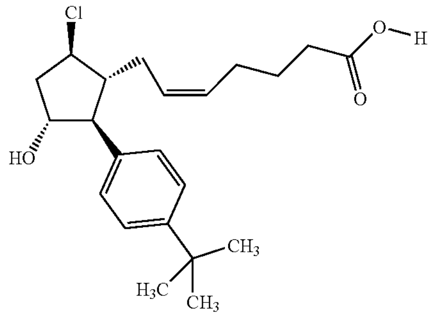 | | | | NA | >10 K | 118 | 2053 | >10 K | 1269 | NA | >10 K |
| 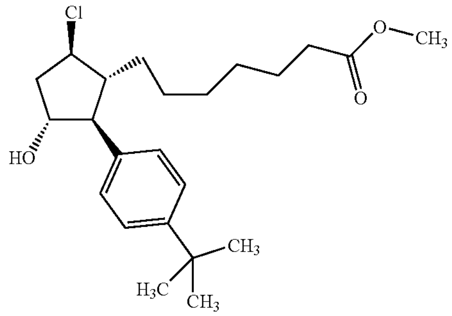 | | | | NA | NA | >10 K | NA | NA | NA | NA | NA |
| 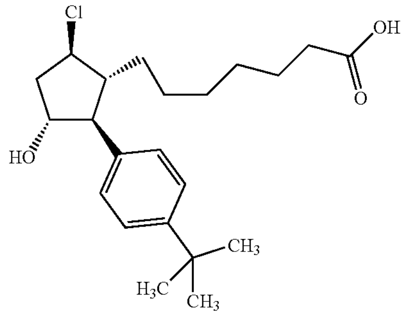 | | | | NA | >10 K | 264 | >10 K | NA | >10 K | NA | >10 K |
| 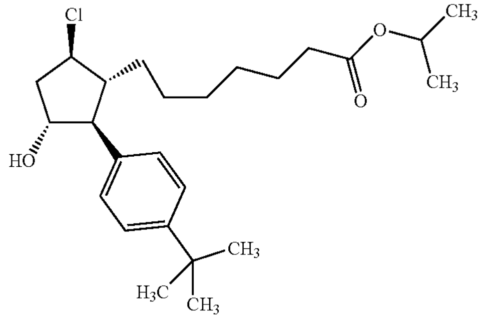 | | | | NA | NA | NA | NA | | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 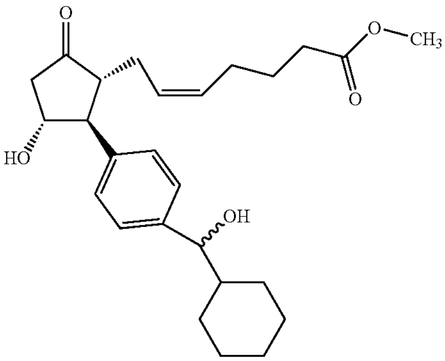 | | | | NA | NA | >10 K | NA | >10 K | NA | NA | NA |
| 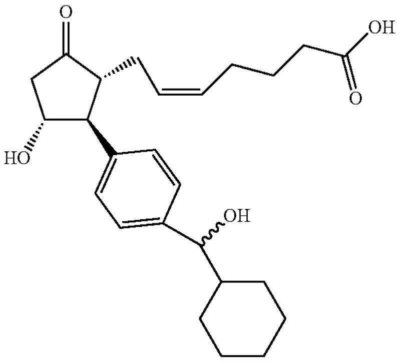 | | | | NA | NA | >10 K | NA | NA | NA | NA | NA |
| 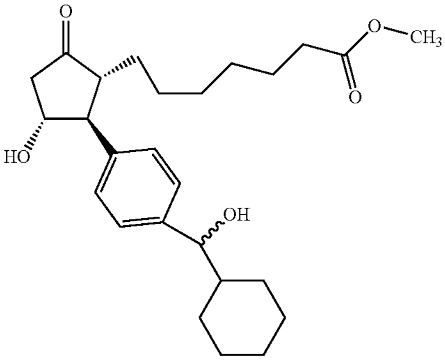 | | | | NA | NA | >10 K | NA | NA | NA | NA | NA |
| 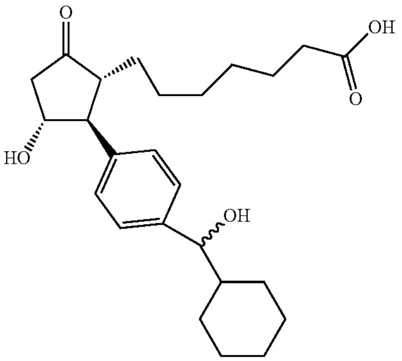 | | | | NA | NA | 450 | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 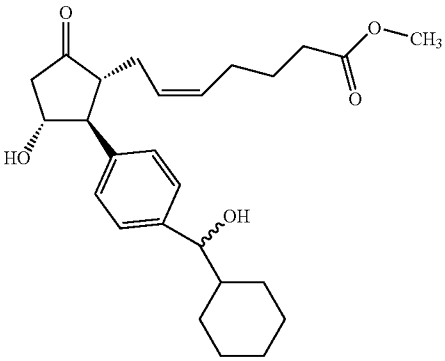 | | | | NA | NA | >10 K | NA | NA | NA | NA | NA |
| 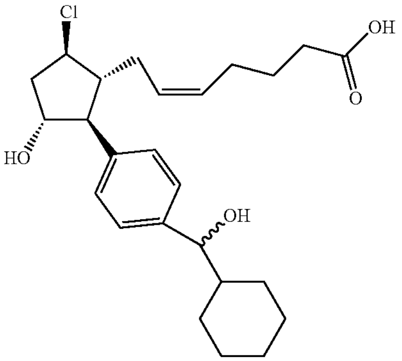 | | | | NA | NA | 392 | NA | NA | NA | NA | NA |
| 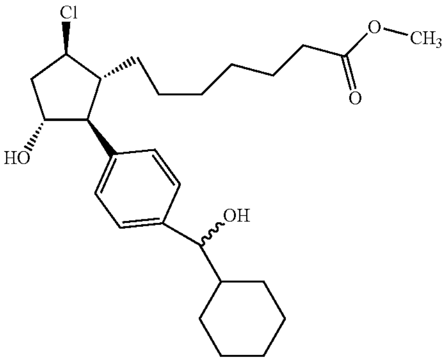 | | | | NA | NA | NA | NA | NA | NA | NA | NA |
| 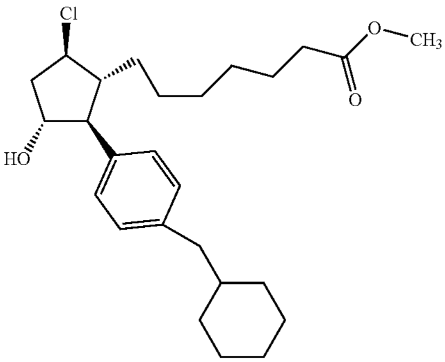 | | | | NA | NA | NA | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 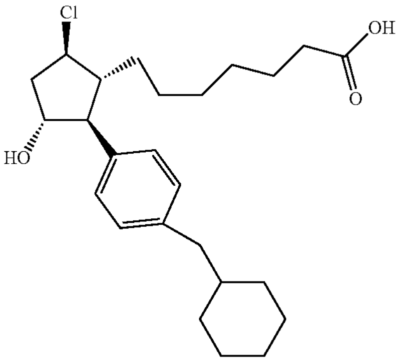 | | | | NA | NA | 3445 | NA | NA | NA | NA | >10 K |
| 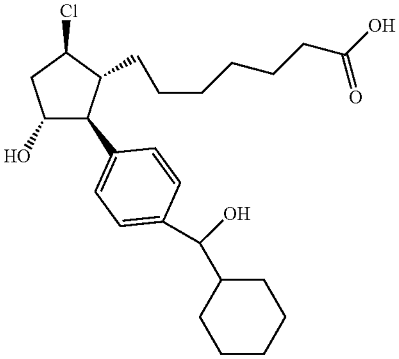 | | | | NA | NA | 2813 | NA | NA | NA | NA | NA |
| 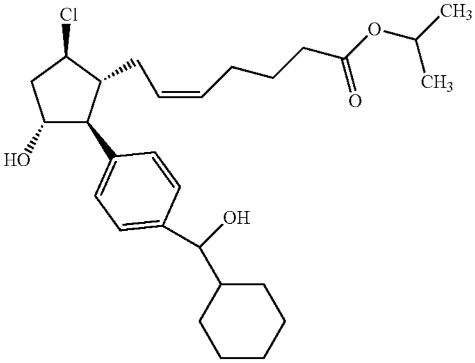 | | | | NA | NA | NA | NA | NA | NA | NA | NA |
| 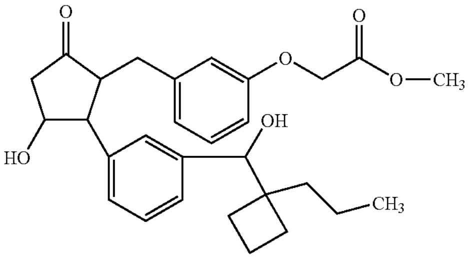 | | | | NA | NA | NA | NA | NA | NA | NA | NA |

-continued
| STRUCTURE | BINDING IC50 (nm) | | | FUNCTIONAL EC50 (nm) | | | | | | | |
|---|---|---|---|---|---|---|---|---|---|---|---|
| | HEP2 | HEP3 | HEP4 | HFP | HEP1 | HEP2 | HEP3A | HEP4 | HTP | HIP | HDP |
| 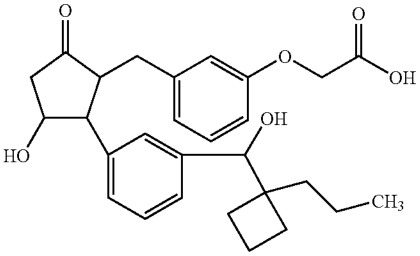 | | | | NA | NA | NA | NA | NA | NA | NA | >10 K |
| 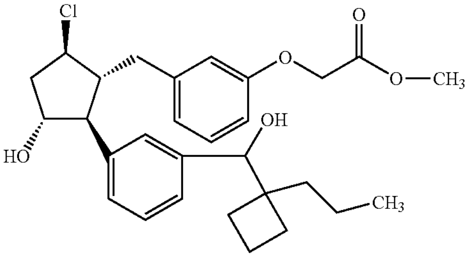 | | | | NA | NA | NA | NA | NA | NA | NA | NA |
| 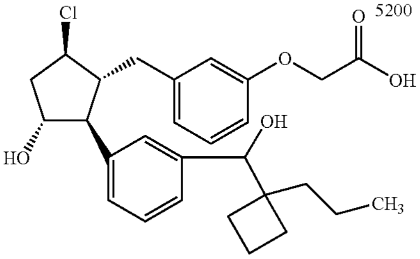 | 5200 | NA | NA | NA | NA | 266 | NA | NA | NA | NA | |
| 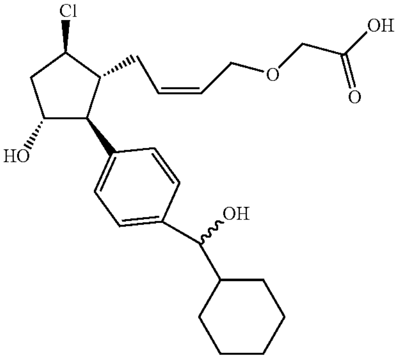 | | | | NA | NA | 3844 | NA | NA | NA | NA | NA |
| 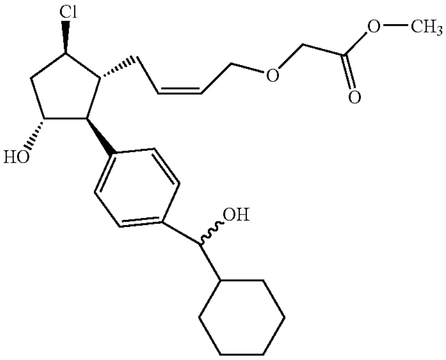 | | | | NA | NA | NA | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 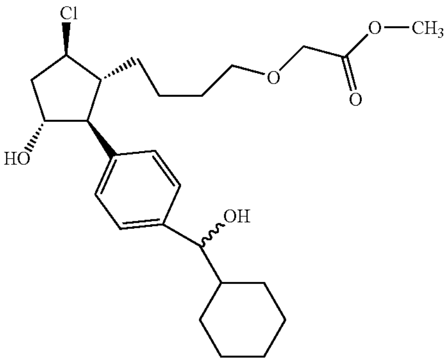 | | | | NA | NA | NA | NA | NA | NA | NA | NA |
| 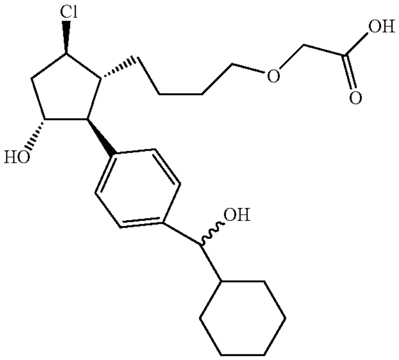 | | | | NA | NA | 20773 | NA | NA | NA | NA | NA |
| 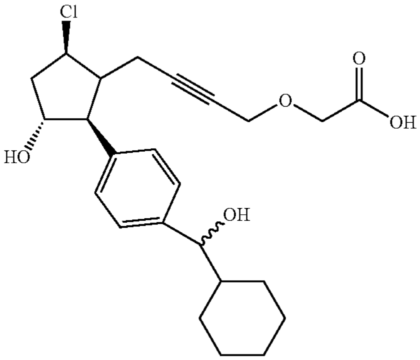 | | | | NA | NA | 1550 | NA | NA | NA | NA | NA |
| 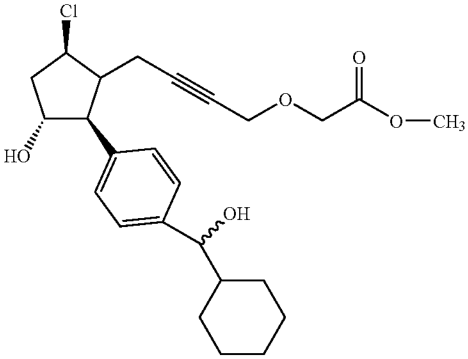 | | | | NA | NA | NA | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 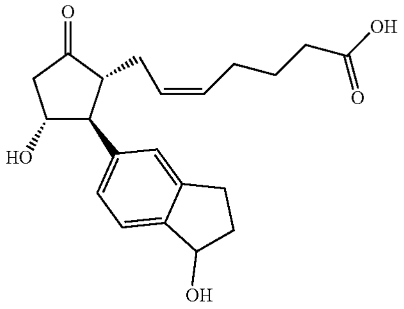 | | | | NA | NA | | NA | NA | NA | NA | NA |
| 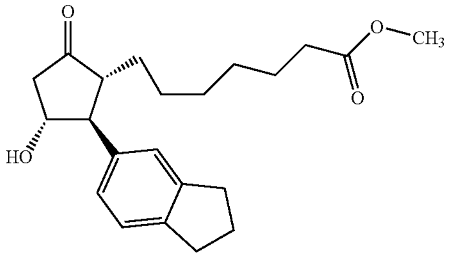 | | | | NA | NA | >10 K | >10 K | >10 K | >10 K | NA | NA |
| 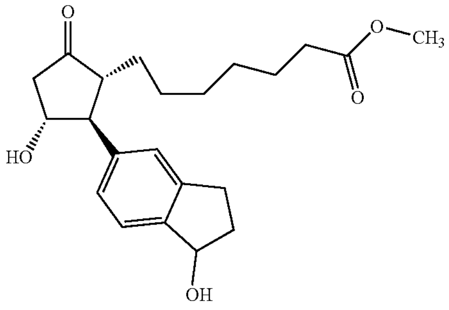 | | | | NA | NA | NA | NA | NA | NA | NA | NA |
| 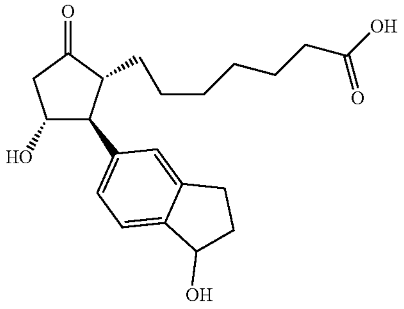 | | | | NA | NA | | NA | NA | >10 K | NA | NA |
| 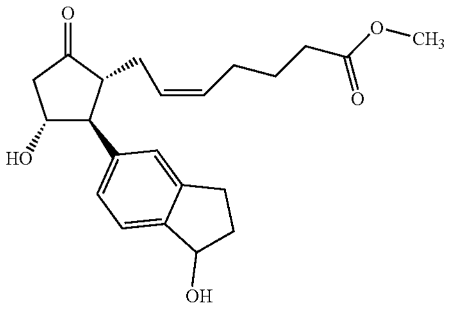 | | | | NA | NA | NA | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 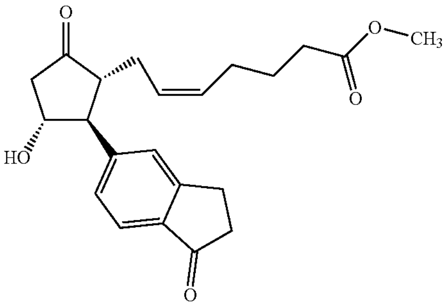 | | | | NA | NA | NA | NA | NA | NA | NA | NA |
| 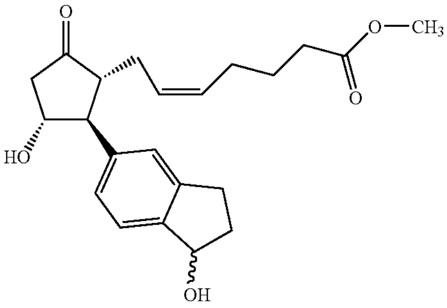 | | | | | | NA | | NA | | | |
| 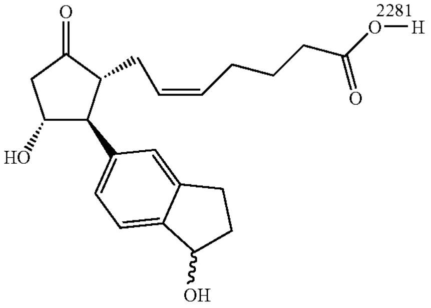 | 2281 | | | NA | NA | 405 | NA | NA | NA | NA | NA |
| 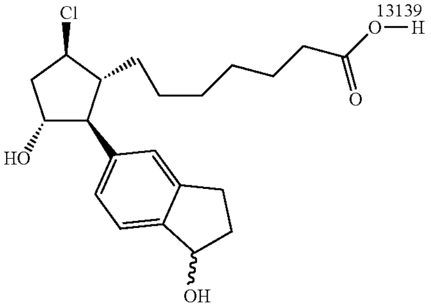 | 13139 | | | NA | NA | 529 | NA | NA | 2993 | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 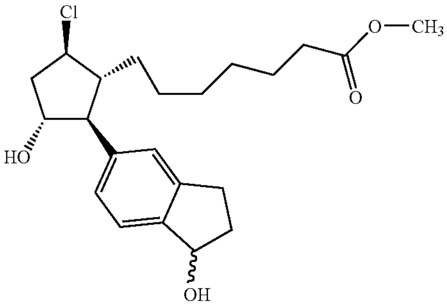 | | | | NA | NA | NA | NA | 22457 | 17525 | NA | NA |
| 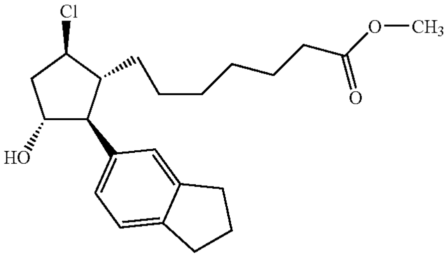 | | | 13100 | NA | NA | NA | NA | NA | 506 | NA | NA |
| 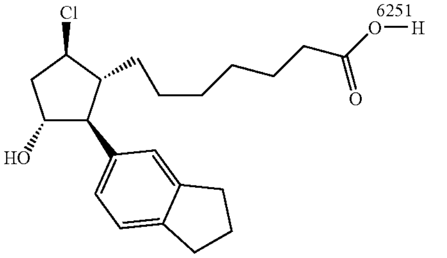 | 6251 | | | NA | 221 | 818 | NA | NA | 200 | NA | |
| 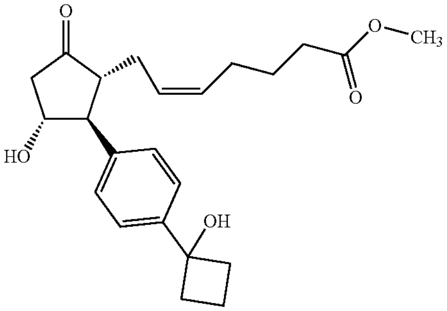 | | | | NA | NA | NA | NA | NA | NA | NA | NA |
| 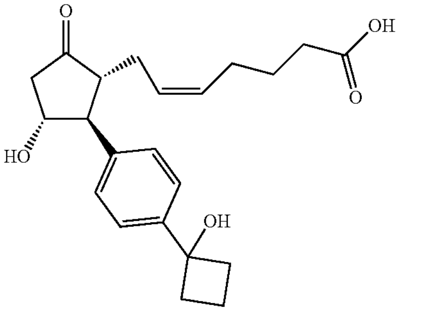 | | | | NA | NA | >10 K | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 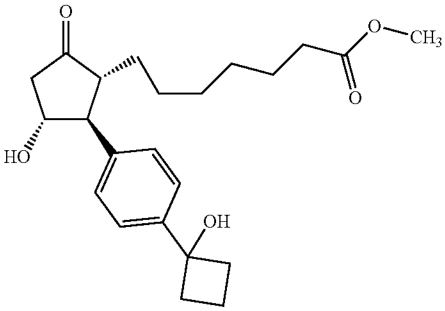 | | | | NA | NA | NA | NA | NA | NA | NA | NA |
| 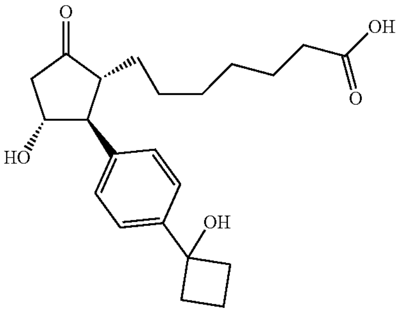 | | | | NA | NA | >10 K | NA | NA | NA | >10 K | NA |
| 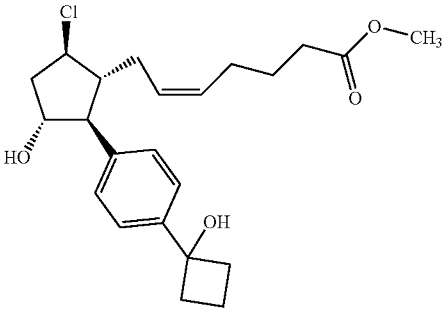 | | | | NA | NA | >10 K | NA | NA | NA | NA | NA |
| 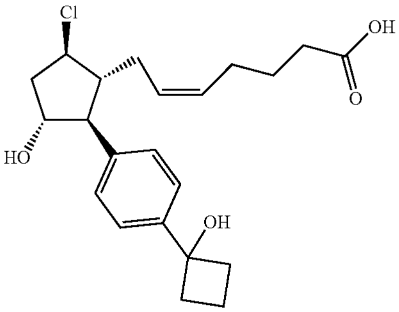 | | | | NA | NA | 513 | NA | NA | >10 K | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 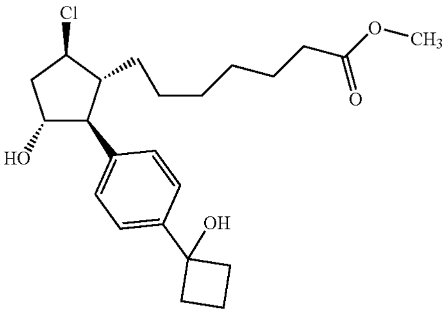 | | | | NA | NA | >10 K | NA | NA | >10 K | NA | NA |
| 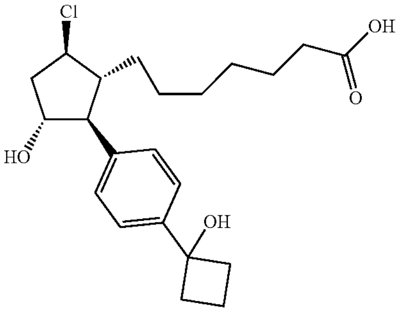 | | | | NA | NA | 743 | NA | NA | >10 K | NA | NA |
| 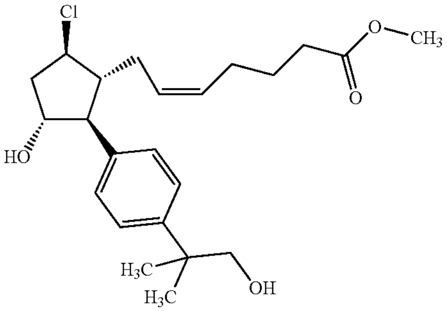 | | | | | | NA | | >10 K | | | |
| 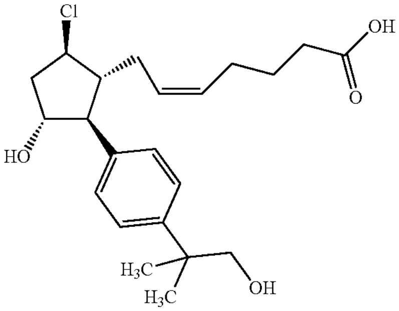 | | | | NA | NA | >10 K | NA | | NA | NA | NA |

-continued
| | BINDING IC50 (nm) | | | FUNCTIONAL EC50 (nm) | | | | | | | |
|---|---|---|---|---|---|---|---|---|---|---|---|
| STRUCTURE | HEP2 | HEP3 | HEP4 | HFP | HEP1 | HEP2 | HEP3A | HEP4 | HTP | HIP | HDP |
| 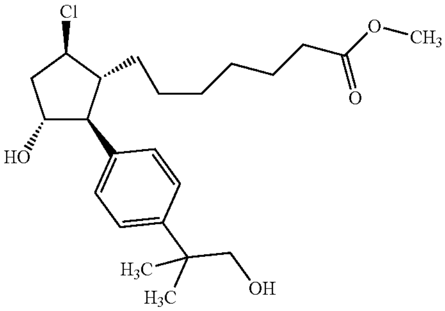 | | | | NA | NA | >10 K | NA | 26289 | NA | NA | NA |
| 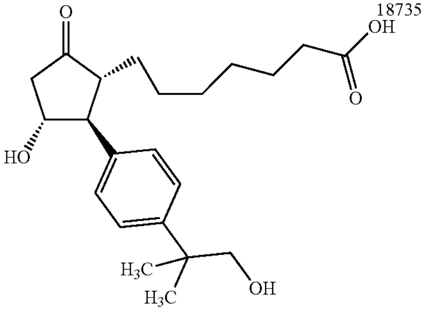 | 18735 | | | NA | NA | 526 | NA | | NA | NA | NA |
| 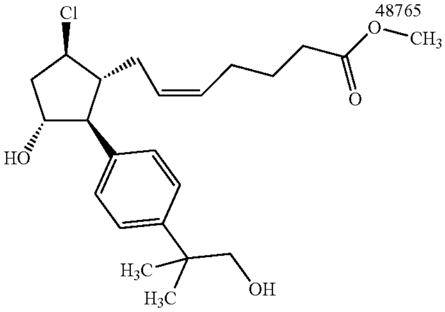 | 48765 | | | | | >10 K | | >10 K | | | |
| 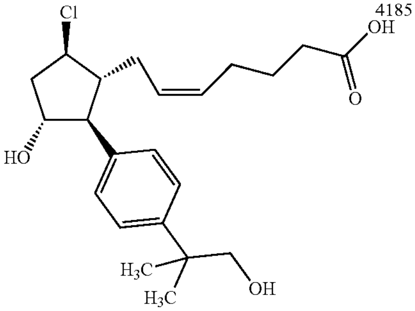 | 4185 | | | NA | NA | 173 | NA | | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 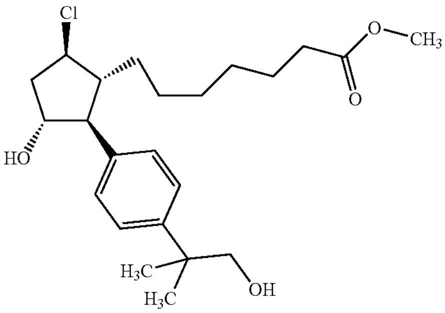 | | | | | | >10 K | | >10 K | | | |
| 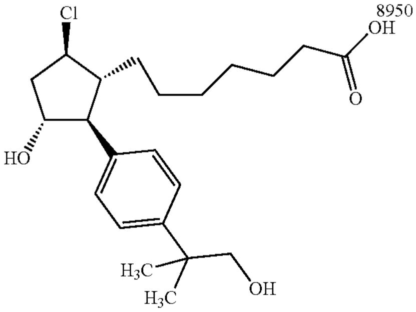 | 8950 | | | NA | NA | 708 | NA | >10 K | NA | NA | NA |
| 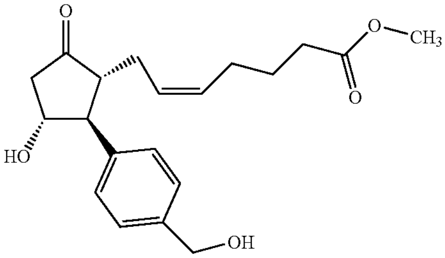 | | | | | | NA | | NA | | | |
| 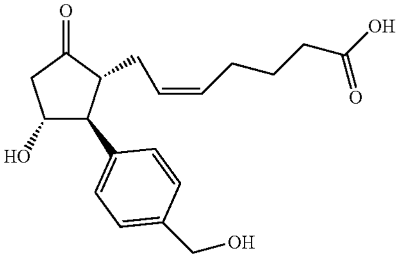 | | | | | | NA | | NA | | | |
| 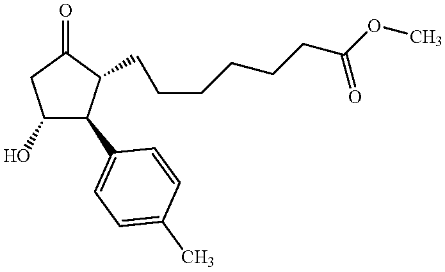 | | | | NA | NA | >10 K | NA | NA | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 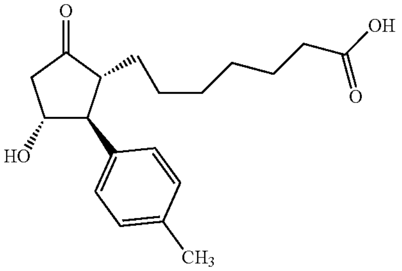 | | | | NA | 1873 | 3128 | NA | NA | 94 | NA | NA |
| 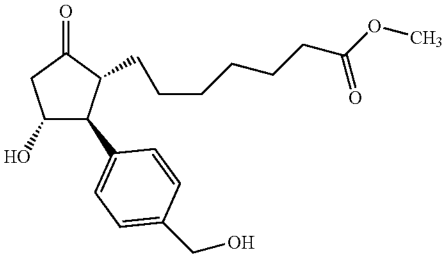 | | | | | | NA | | NA | | | |
| 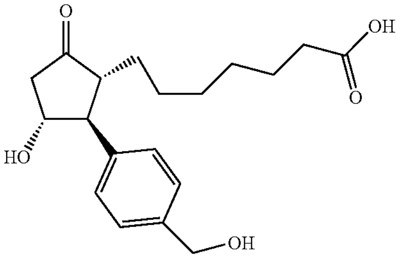 | | | | | | NA | | NA | | | |
| 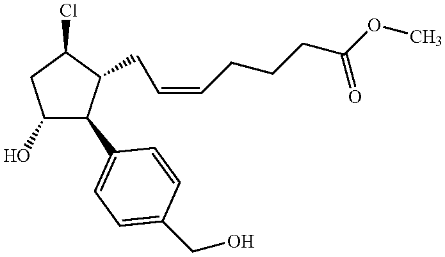 | | | | | | >10 K | | NA | | | |
| 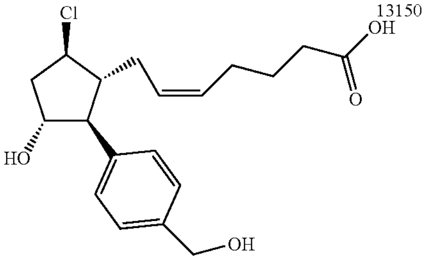 | 13150 | | | NA | NA | | NA | NA | NA | NA | NA |

-continued
| | BINDING IC50 (nm) | | | FUNCTIONAL EC50 (nm) | | | | | | | |
|---|---|---|---|---|---|---|---|---|---|---|---|
| STRUCTURE | HEP2 | HEP3 | HEP4 | HFP | HEP1 | HEP2 | HEP3A | HEP4 | HTP | HIP | HDP |
| 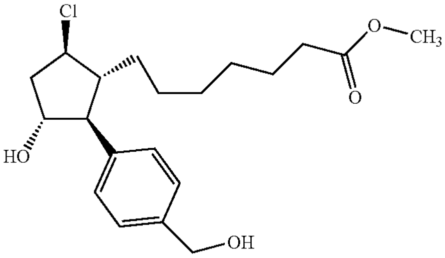 | | | | | | NA | | >10 K | | | |
| 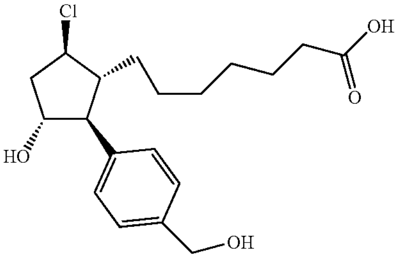 | | | | | | >10 K | | NA | | | |
| 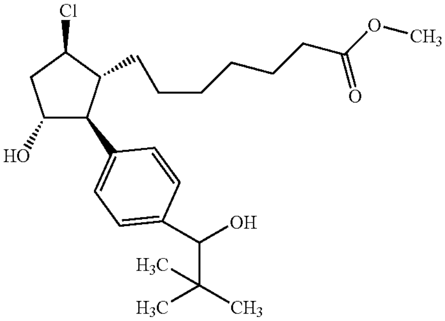 | | | | NA | NA | 4995 | NA | >10 K | NA | NA | NA |
| 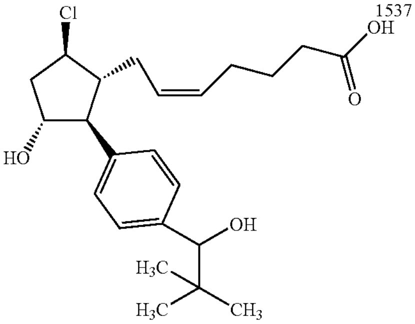 | 1537 | | | NA | NA | 779 | NA | >10 K | NA | NA | NA |
| 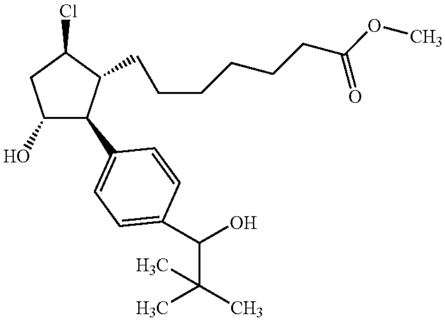 | | | | NA | NA | 6575 | NA | >10 K | NA | NA | NA |

-continued
| STRUCTURE | BINDING IC50 (nm) HEP2 | HEP3 | HEP4 | FUNCTIONAL EC50 (nm) HFP | HEP1 | HEP2 | HEP3A | HEP4 | HTP | HIP | HDP |
|---|---|---|---|---|---|---|---|---|---|---|---|
| 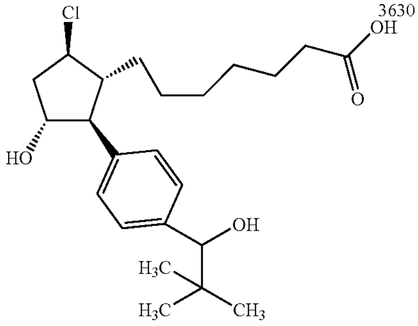 | 3630 | | | NA | NA | 1265 | NA | >10 K | NA | NA | NA |
| 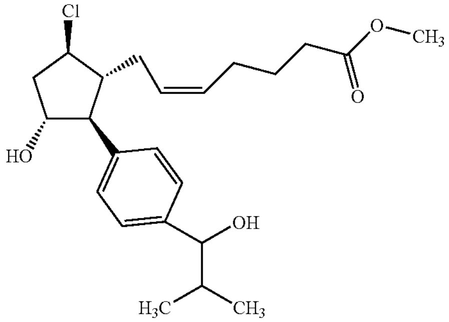 | | | | | | >10 K | | >10 K | | | |
| 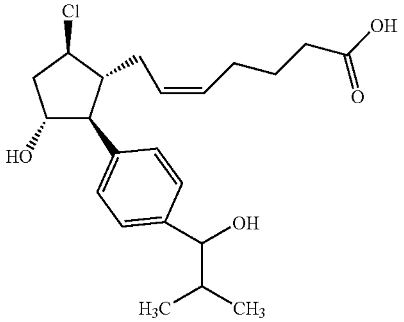 | | Ki 1340 | | NA | NA | 497 | NA | NA | NA | NA | NA |
| 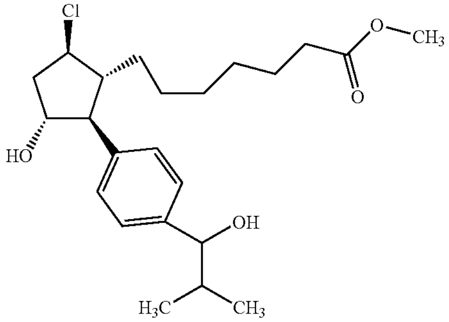 | | | | | | >10 K | | >10 K | | | |

-continued
| | BINDING IC50 (nm) | | | FUNCTIONAL EC50 (nm) | | | | | | | |
|---|---|---|---|---|---|---|---|---|---|---|---|
| STRUCTURE | HEP2 | HEP3 | HEP4 | HFP | HEP1 | HEP2 | HEP3A | HEP4 | HTP | HIP | HDP |
| 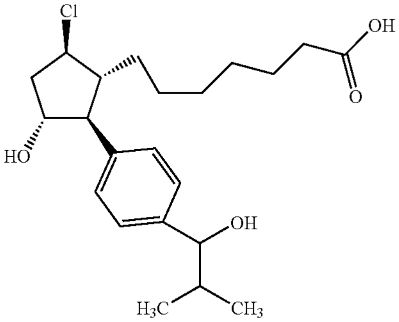 | | Ki 3022 | | | | >10 K | | NA | | | |

| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 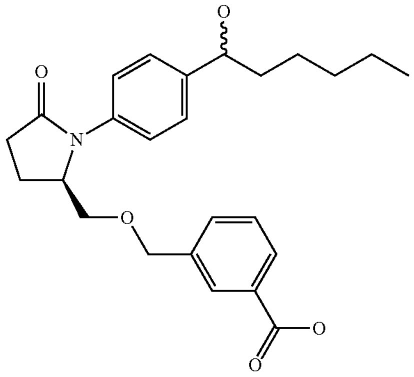 | >10000 | 517 | NA | | NA | >10000 | NA | NA | NA | NA | NA | NA |
| 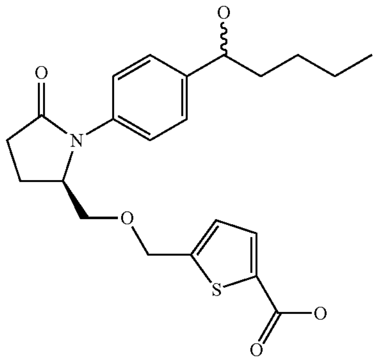 | 212 | 8 | 387 | | NA | >10000 | NA | NA | NA | NA | NA | NA |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 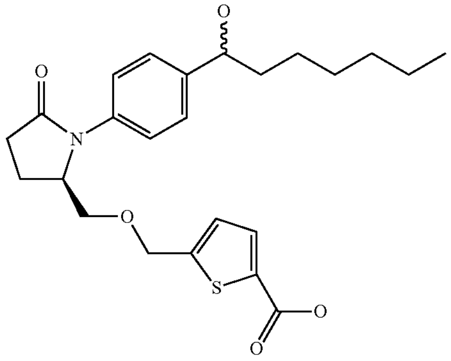 | 20 | 1.5 | 190 | | NA | >10000 | NA | NA | NA | NA | NA | 5763 |
| 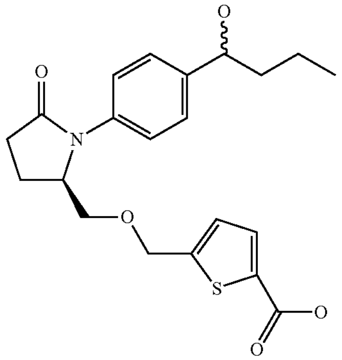 | 426 | 27 | 1639 | | NA | >10000 | NA | NA | NA | NA | NA | NA |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 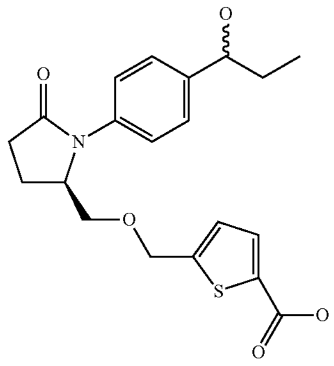 | 1812 | 312 | 5731 | | >10000 | >10000 | NA | NA | NA | NA | NA | 7560 |
| 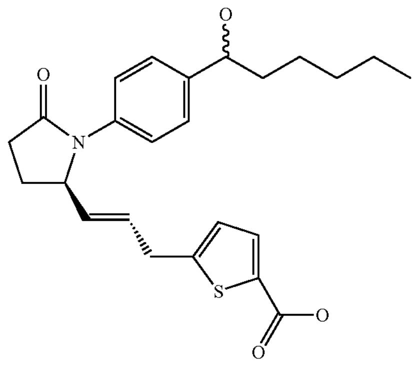 | 226 | 15 | 1382 | | NA | >10000 | NA | NA | NA | NA | NA | NA |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 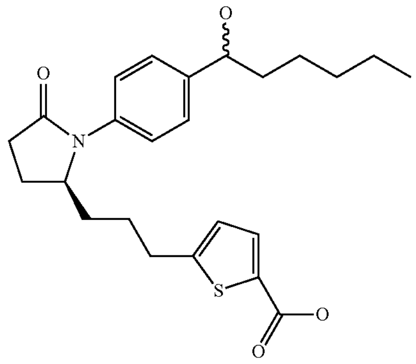 | 5 | 0.55 | 23 | | NA | >10000 | NA | NA | 155 | NA | NA | 1234 |
| 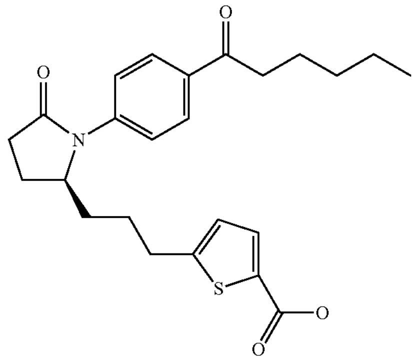 | 16 | 1.6 | 31 | | >10000 | >10000 | NA | NA | 2345 | NA | NA | 7695 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 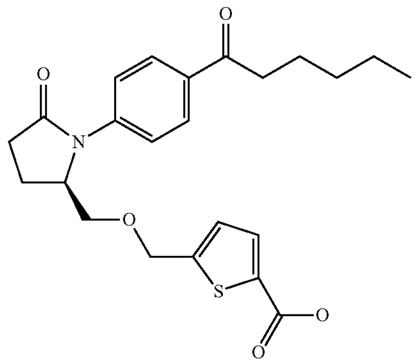 | 215 | 8 | 163 | | NA | >10000 | NA | NA | NA | NA | NA | NA |
| 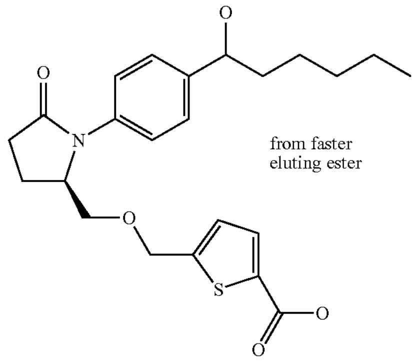 from faster eluting ester | 62 | 5 | 345 | | >10000 | >10000 | NA | NA | 153 | NA | NA | 7749 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 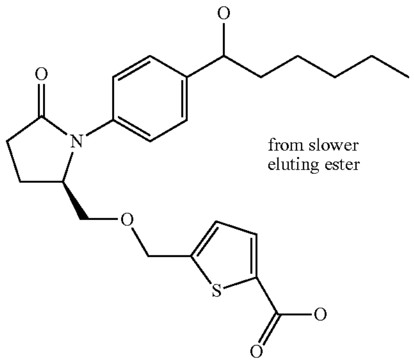 from slower eluting ester | 15 | 1.5 | 116 | | >10000 | 6032 | NA | NA | 1205 | NA | NA | 6800 |
| 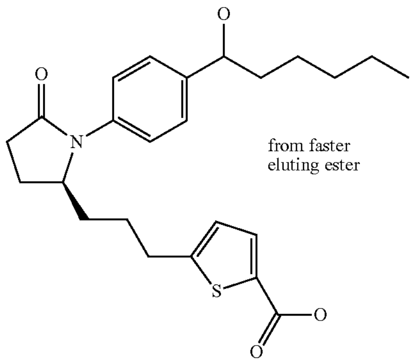 from faster eluting ester | 6 | 0.19 | 21 | | >10000 | >10000 | NA | NA | 12 | NA | NA | 812 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 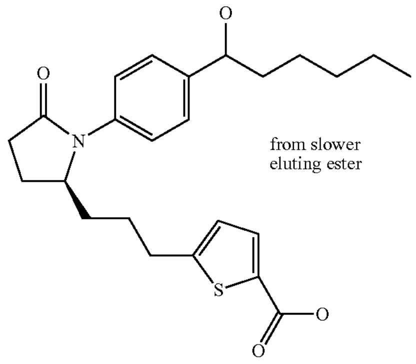 from slower eluting ester | 1.6 | 0.15 | 15 | | >10000 | 4849 | NA | NA | 156 | NA | NA | 296 |
| 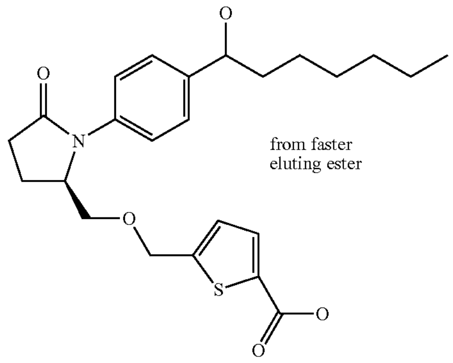 from faster eluting ester | 134 | 7 | 229 | | NA | 3842 | NA | NA | 71 | NA | NA | 6829 |

-continued
| Structure | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| | EC50 | EC50 | Ki | 6.0 | EC50 | KI | hFP | hEP1 | hEP3A | hTP | hIP | hDP |
| 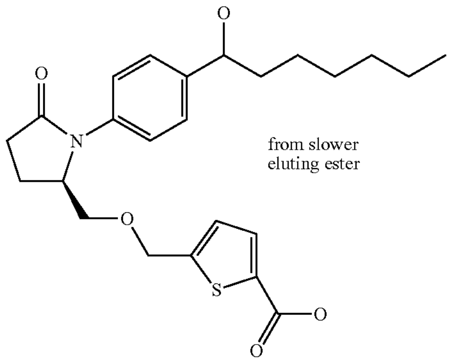 from slower eluting ester | 49 | 4 | 201 | | NA | 3288 | NA | NA | 621 | NA | NA | NA |
| 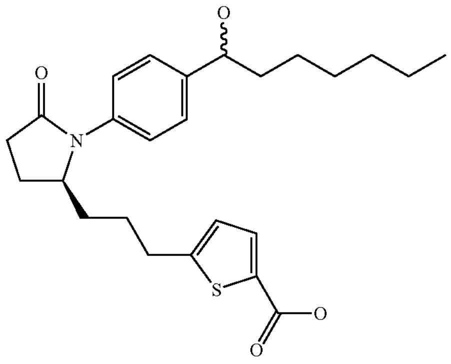 | 30 | 0.9 | 10 | | >10000 | | NA | NA | 47 | NA | NA | 105 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 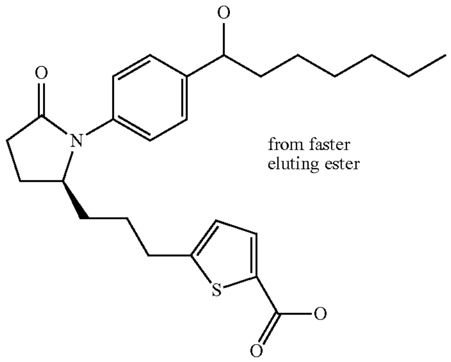 from faster eluting ester | 16 | 1.4 | 12 | | NA | | NA | 6952 | 7 | NA | NA | 37 |
| 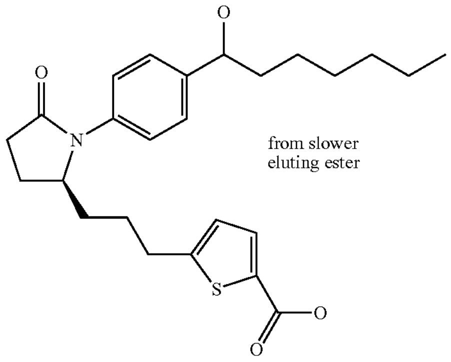 from slower eluting ester | 5 | 0.6 | 8 | | NA | | NA | NA | 33 | NA | >10000 | 106 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 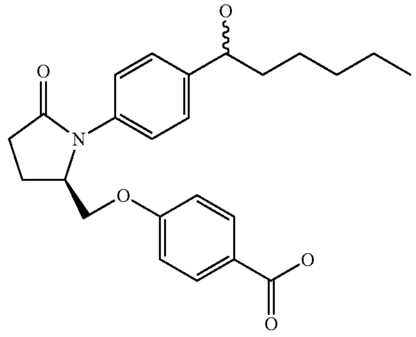 | 728 | NA | 22726 | | NA | 8752 | NA | NA | NA | NA | NA | NA |
| 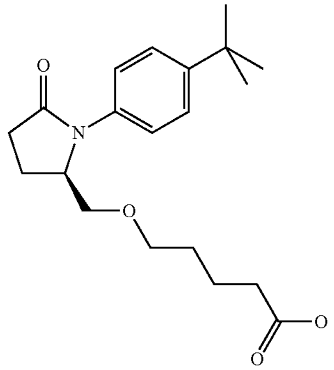 | >10000 | | NA | | >10000 | >10000 | | | | | | |

-continued
| Structure | EP2 data flipr EC50 | EP2 data cAMP EC50 | EP2 data Ki | EP2 data Ki pH 6.0 | EP4 data flipr EC50 | EP4 data KI | Other Receptors (EC50 in nM) hFP | hEP1 | hEP3A | hTP | hIP | hDP |
|---|---|---|---|---|---|---|---|---|---|---|---|---|
| 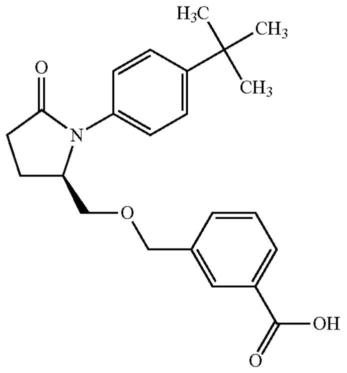 | >10000 | | NA | | >10000 | >10000 | | | | | | |
| 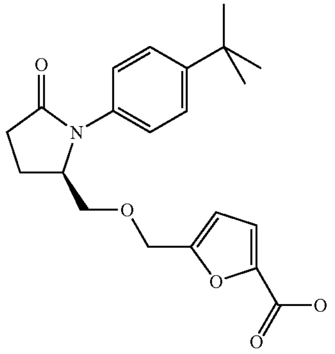 | 442 | 28 | 4000 | 189 | >10000 | >10000 | NA | NA | >10000 | NA | NA | 1921 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 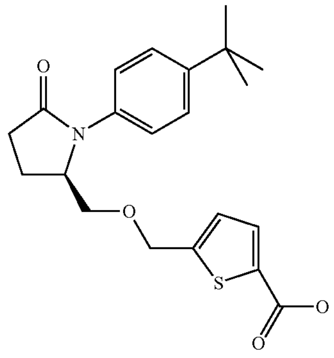 | 1343 | 51 | 501 | 27 | >10000 | >10000 | NA | >10000 | 19234 | >10000 | NA | 2323 |
| 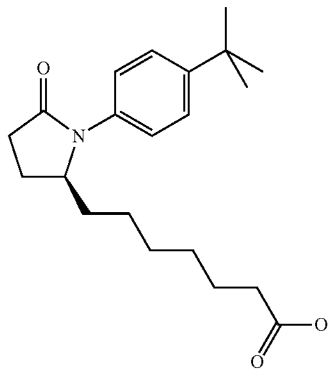 | 4121 | 548 | >10000 | | >10000 | >10000 | NA | >10000 | 19544 | NA | NA | >10000 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 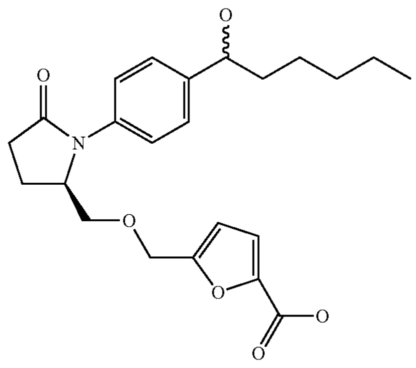 | 388 | 26 | 2028 | | NA | >10000 | NA | NA | 1927 | NA | NA | NA |
| 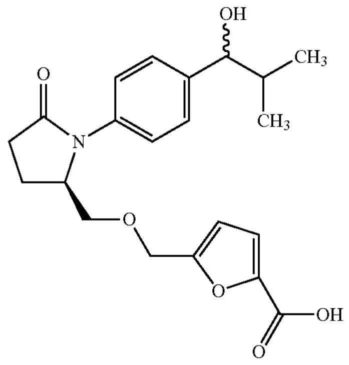 | 7669 | 1218 | >10000 | | NA | >10000 | NA | NA | NA | NA | NA | NA |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 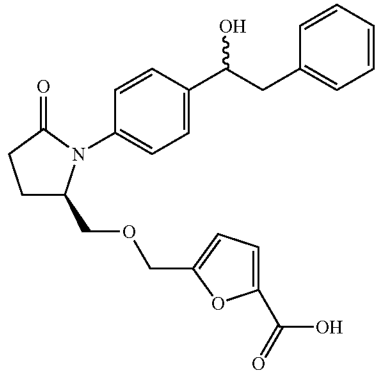 | 1228 | 148 | 2293 | | NA | >10000 | NA | NA | NA | NA | NA | NA |
| 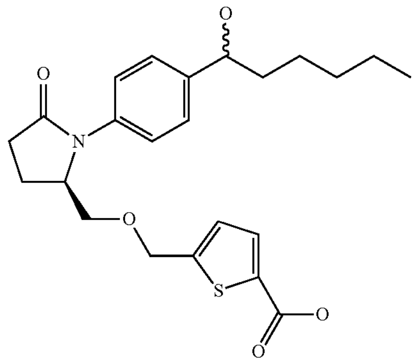 | 8 | 3 | 115 | | >10000 | >10000 | NA | NA | 403 | NA | NA | 3233 |

-continued
| Structure | EP2 data flipr EC50 | cAMP EC50 | Ki | Ki pH 6.0 | EP4 data flipr EC50 | KI | Other Receptors (EC50 in nM) hFP | hEP1 | hEP3A | hTP | hIP | hDP |
|---|---|---|---|---|---|---|---|---|---|---|---|---|
| 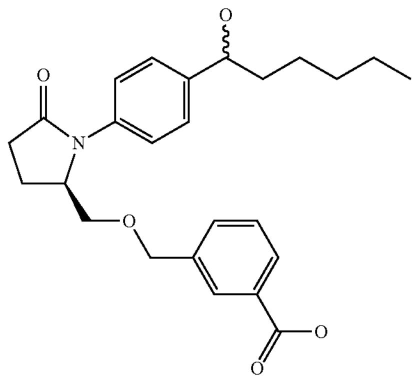 | >10000 | 517 | NA | | NA | >10000 | NA | NA | NA | NA | NA | NA |
| 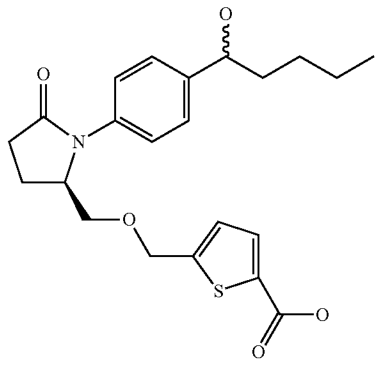 | 212 | 8 | 387 | | NA | >10000 | NA | NA | NA | NA | NA | NA |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 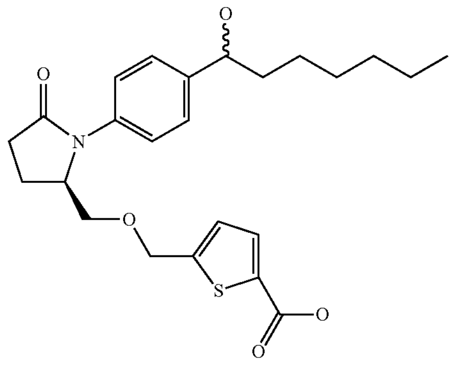 | 20 | 1.5 | 190 | | NA | >10000 | NA | NA | 519 | NA | NA | 5763 |
| 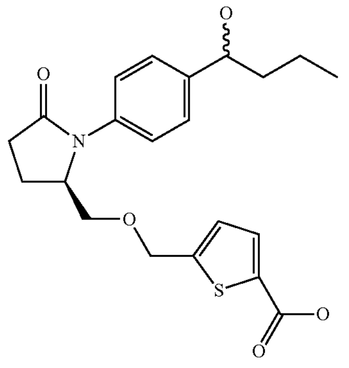 | 426 | 27 | 1639 | | NA | >10000 | NA | NA | NA | NA | NA | NA |

-continued
| Structure | EP2 data flipr EC50 | cAMP EC50 | Ki | Ki pH 6.0 | EP4 data flipr EC50 | KI | Other Receptors (EC50 in nM) hFP | hEP1 | hEP3A | hTP | hIP | hDP |
|---|---|---|---|---|---|---|---|---|---|---|---|---|
| 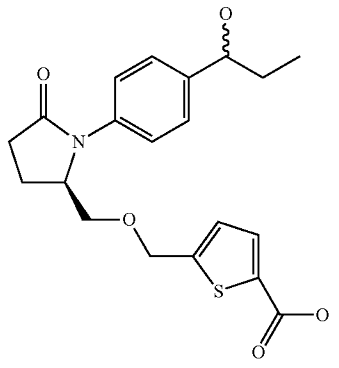 | 1812 | 312 | 5731 | | >10000 | >10000 | NA | NA | NA | NA | NA | 7560 |
| 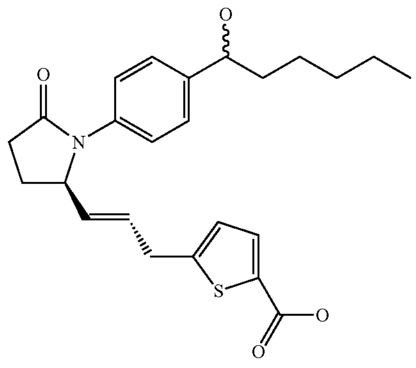 | 226 | 15 | 1382 | | NA | >10000 | NA | NA | 1411 | NA | NA | NA |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 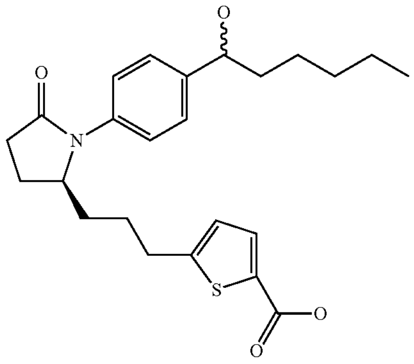 | 5 | 0.55 | 23 | | NA | >10000 | NA | NA | 155 | NA | NA | 1234 |
| 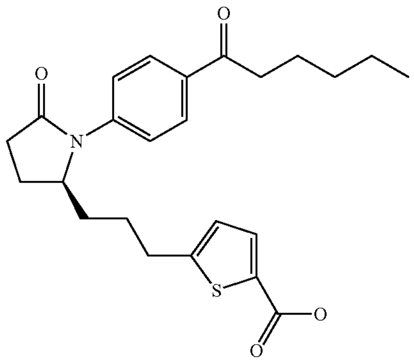 | 16 | 1.6 | 31 | | >10000 | >10000 | NA | NA | 2345 | NA | NA | 7695 |

-continued
| Structure | EP2 data flipr EC50 | EP2 data cAMP EC50 | EP2 data Ki | EP2 data Ki pH 6.0 | EP4 data flipr EC50 | EP4 data KI | Other Receptors (EC50 in nM) hFP | hEP1 | hEP3A | hTP | hIP | hDP |
|---|---|---|---|---|---|---|---|---|---|---|---|---|
| 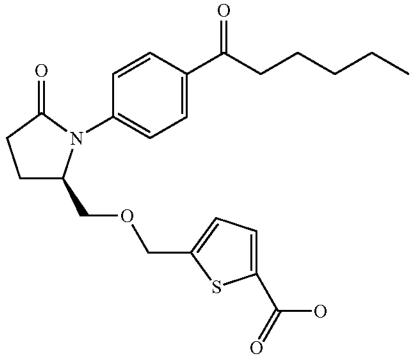 | 215 | 8 | 163 | | NA | >10000 | NA | NA | NA | NA | NA | NA |
| 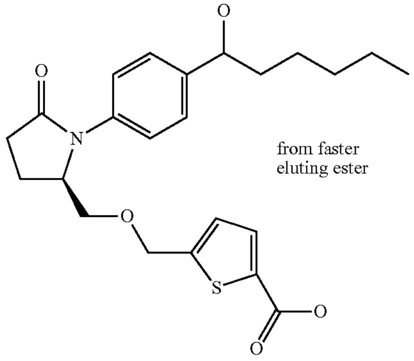 from faster eluting ester | 62 | 5 | 345 | | >10000 | >10000 | NA | NA | 153 | NA | NA | 7749 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 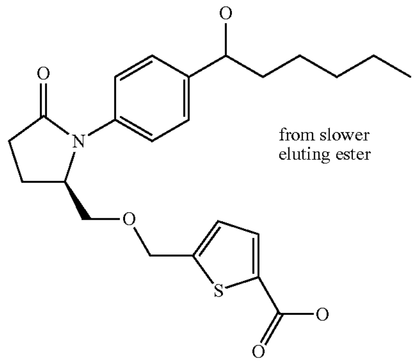 from slower eluting ester | 15 | 1.5 | 116 | | >10000 | 6032 | NA | NA | 1205 | NA | NA | 6800 |
| 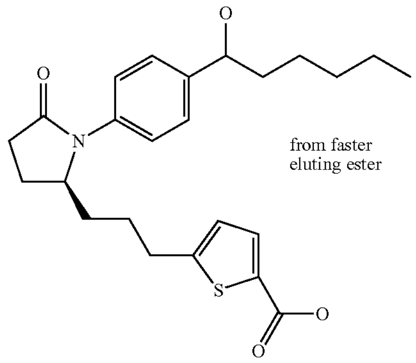 from faster eluting ester | 6 | 0.19 | 21 | | >10000 | >10000 | NA | NA | 12 | NA | NA | 812 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 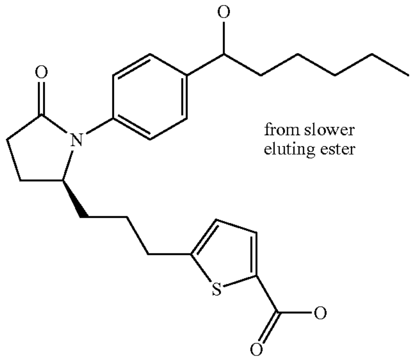 from slower eluting ester | 1.6 | 0.15 | 15 | | >10000 | 4849 | NA | NA | 156 | NA | NA | 296 |
| 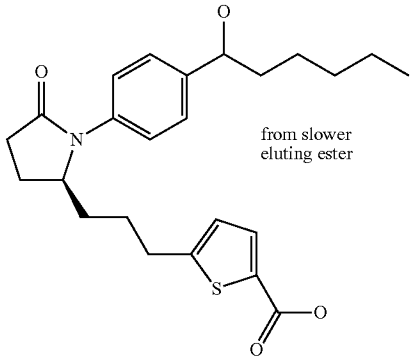 from slower eluting ester | 134 | 7 | 229 | | NA | 3842 | NA | NA | 71 | NA | NA | 6829 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 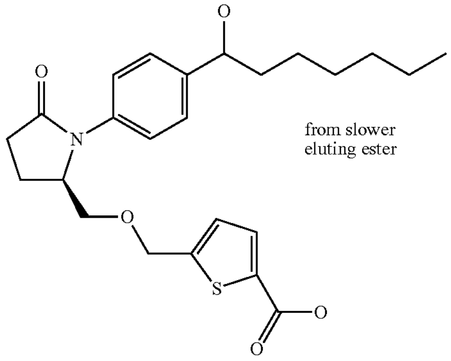 from slower eluting ester | 49 | 4 | 201 | | NA | 3288 | NA | NA | 621 | NA | NA | NA |
| 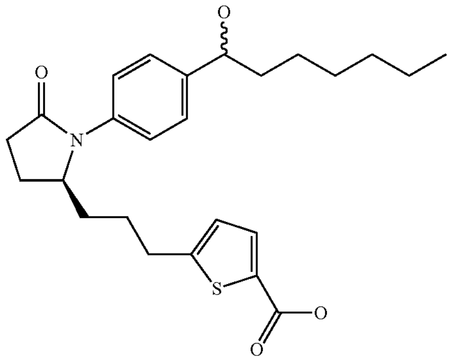 | 30 | 0.9 | 10 | | >10000 | | NA | NA | 47 | NA | NA | 105 |

-continued
| Structure | EP2 data | | | | EP4 data | | | | | | | |
|---|---|---|---|---|---|---|---|---|---|---|---|---|
| | flipr | cAMP | | Ki pH | flipr | | Other Receptors (EC50 in nM) | | | | | |
| | EC50 | EC50 | Ki | 6.0 | EC50 | KI | hFP | hEP1 | hEP3A | hTP | hIP | hDP |
| 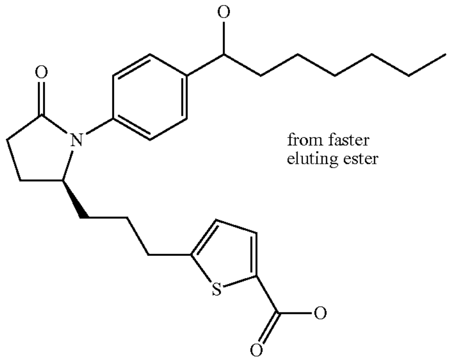 from faster eluting ester | 16 | 1.4 | 12 | | NA | | NA | 6952 | 7 | NA | NA | 37 |
| 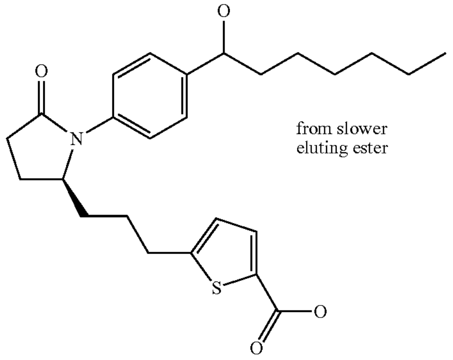 from slower eluting ester | 5 | 0.6 | 8 | | NA | | NA | NA | 33 | NA | >10000 | 106 |

-continued
| | EP2 data | | | | | | | | | | | |
|---|---|---|---|---|---|---|---|---|---|---|---|---|
| | | | | Ki | EP4 data | | | | | | | |
| | flipr | cAMP | | pH | flipr | | Other Receptors (EC50 in nM) | | | | | |
| Structure | EC50 | EC50 | Ki | 6.0 | EC50 | KI | hFP | hEP1 | hEP3A | hTP | hIP | hDP |
| 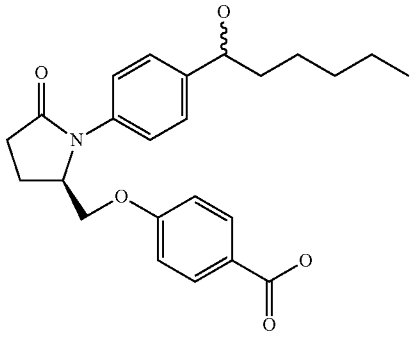 | 7284 | NA | 22726 | | NA | 8752 | NA | NA | NA | NA | NA | NA |

| | | | | | | | | | | | |
|---|---|---|---|---|---|---|---|---|---|---|---|
| | | | | | | | FUNCTIONAL (Ca2+, EC50, nM) | | | | |
| | BINDING (K$_i$, nM) | | | | | | | | HE | | |
| STRUCTURE | HE P2 | HE P3 | HE P4 | HF P | HE P1 | HE P2 | P3 A | HE P4 | HT P | HIP | HD P |
| 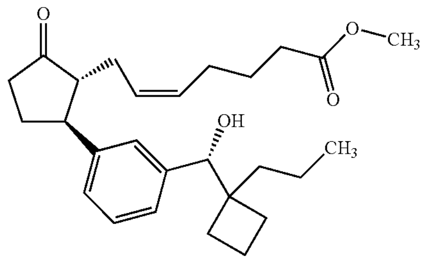 | | | | NA | NA | NA | NA | NA | >10K | NA | NA |
| 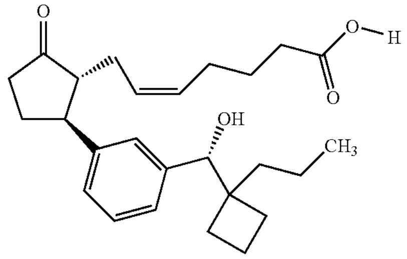 | | | | NA | NA | 2657 | 2789 | NA | NA | NA | NA |
| 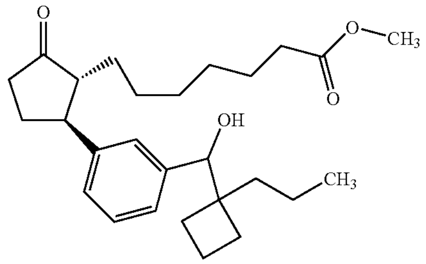 | | | | NA | NA | NA | NA | NA | NA | NA | NA |
| 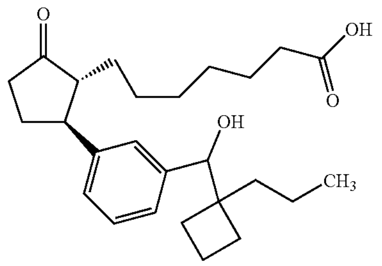 | | | | NA | NA | 3407 | 3828 | NA | NA | NA | NA |
| 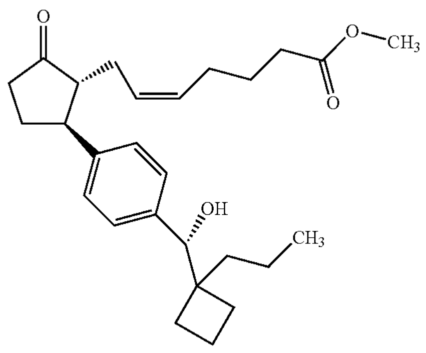 | | | | NA | NA | NA | NA | NA | NA | NA | NA |

-continued
| | | | | | | | | | | | |
|---|---|---|---|---|---|---|---|---|---|---|---|
| | | | | | | | FUNCTIONAL (Ca2+, EC50, nM) | | | | |
| | BINDING ($K_i$, nM) | | | | | | HE | | | | |
| STRUCTURE | HE P2 | HE P3 | HE P4 | HF P | HE P1 | HE P2 | P3 A | HE P4 | HT P | HIP | HD P |
| 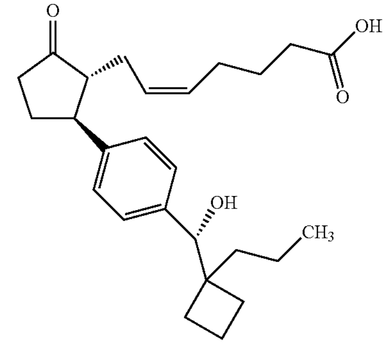 | | | | NA | NA | 287<br>2 | NA | NA | NA | NA | >10<br>K |
| 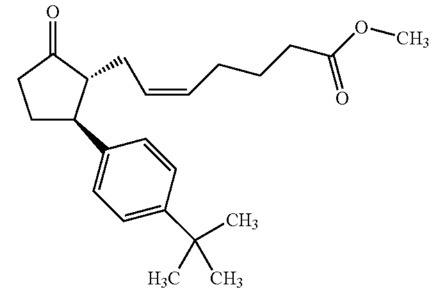 | | | | NA | NA | NA | NA | NA | NA | NA | NA |
| 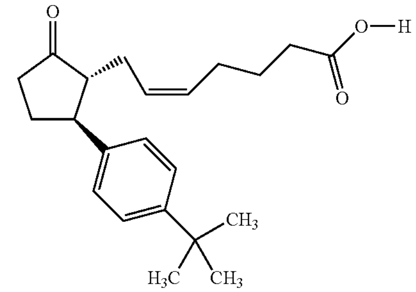 | | | | NA | NA | 105<br>0 | NA | NA | NA | NA | NA |
| 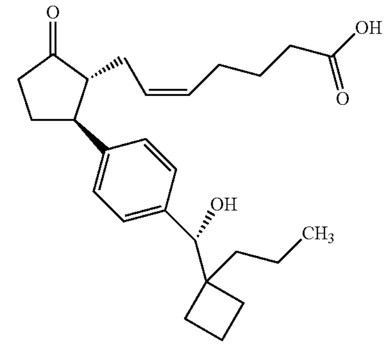 | | | | NA | NA | >10<br>K | NA | >10<br>K | NA | NA | NA |

-continued
| | | | | | | | FUNCTIONAL (Ca2+, EC50, nM) | | | | |
|---|---|---|---|---|---|---|---|---|---|---|---|
| | BINDING ($K_i$, nM) | | | | | | | | HE | | |
| STRUCTURE | HE P2 | HE P3 | HE P4 | HF P | HE P1 | HE P2 | P3 A | HE P4 | HT P | HIP | HD P |
| 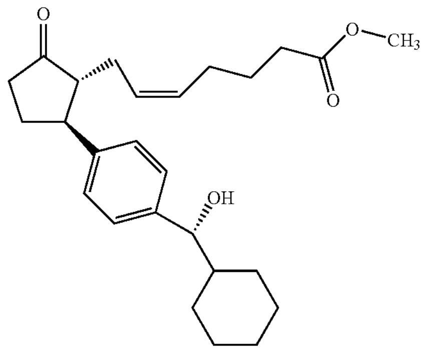 | | | | NA | NA | >10 K | NA | NA | NA | NA | NA |
| 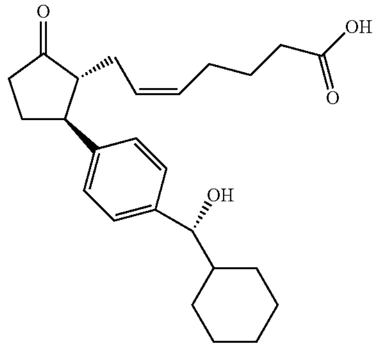 | | | | NA | NA | 164 0 | NA | NA | NA | NA | NA |
| 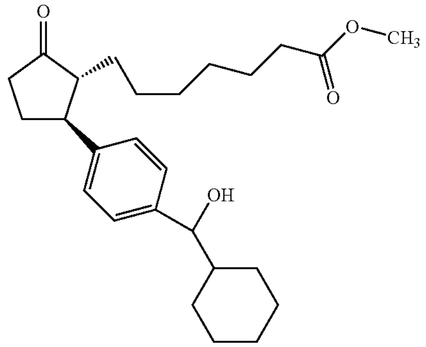 | | | | NA | NA | >10 K | NA | NA | >10 K | NA | NA |
| 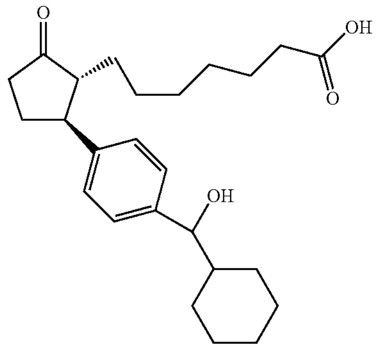 | | | | NA | NA | 204 7 | NA | NA | NA | NA | NA |

-continued
| | BINDING ($K_i$, nM) | | | | | | FUNCTIONAL (Ca2+, EC50, nM) | | | | |
|---|---|---|---|---|---|---|---|---|---|---|---|
| | | | | | | | | | HE | | |
| STRUCTURE | HE P2 | HE P3 | HE P4 | HF P | HE P1 | HE P2 | P3 A | HE P4 | HT P | HIP | HD P |
| 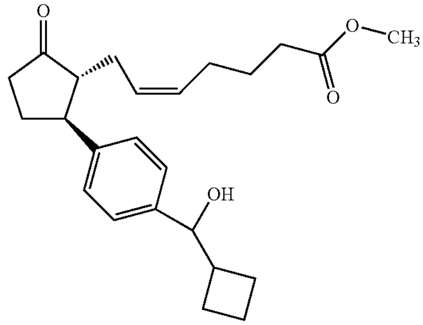 | | | | NA | NA | NA | NA | NA | NA | NA | NA |
| 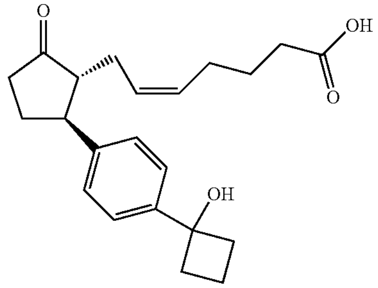 | | | | NA | NA | NA | NA | NA | NA | NA | NA |
| 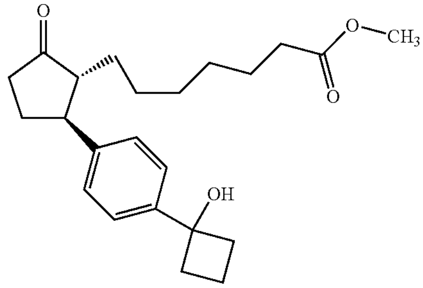 | | | | NA | NA | NA | NA | NA | NA | NA | NA |
| 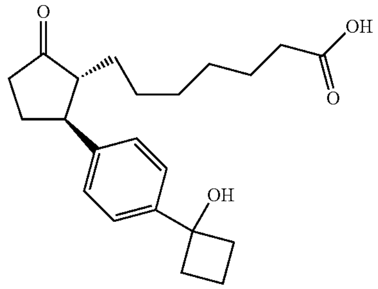 | | | | NA | NA | >10 K | NA | NA | NA | NA | NA |

-continued
| | | | | | | | | | | | |
|---|---|---|---|---|---|---|---|---|---|---|---|
| | | | | | | | FUNCTIONAL (Ca2+, EC50, nM) | | | | |
| | BINDING ($K_i$, nM) | | | | | | | | HE | | |
| STRUCTURE | HE P2 | HE P3 | HE P4 | HF P | HE P1 | HE P2 | P3 A | HE P4 | HT P | HIP | HD P |
| 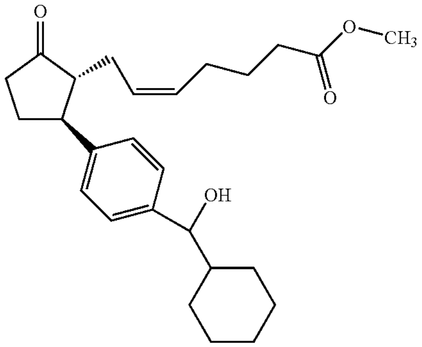 | | | | NA | NA | NA | NA | NA | NA | NA | NA |
| 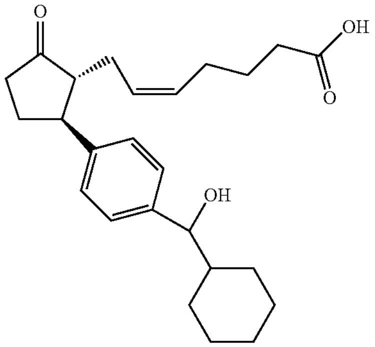 | | | | NA | NA | 210 1 | NA | NA | NA | NA | NA |
| 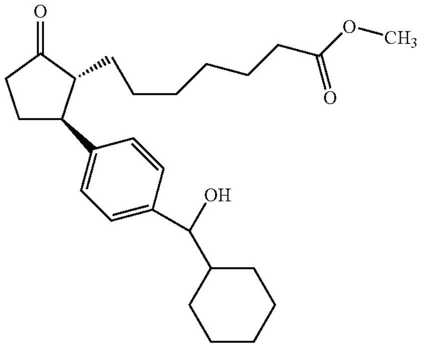 | | | | NA | NA | NA | NA | NA | NA | NA | NA |
| 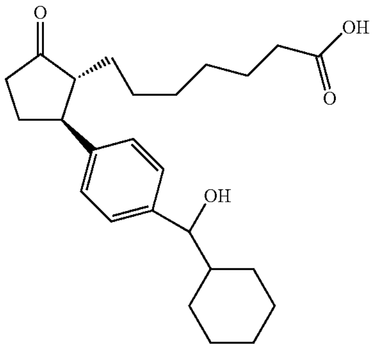 | | | | NA | NA | >10 K | NA | NA | >10 K | NA | NA |

-continued
| STRUCTURE | BINDING ($K_i$, nM) | | | | | | FUNCTIONAL (Ca2+, EC50, nM) HE | | | | |
|---|---|---|---|---|---|---|---|---|---|---|---|
| | HE P2 | HE P3 | HE P4 | HF P | HE P1 | HE P2 | P3 A | HE P4 | HT P | HIP | HD P |
| 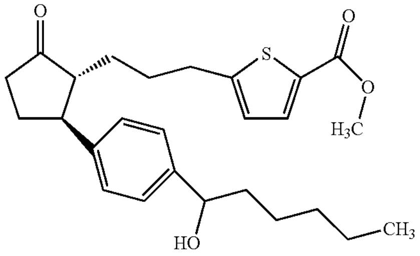 | | | | | | | | | | | |
| 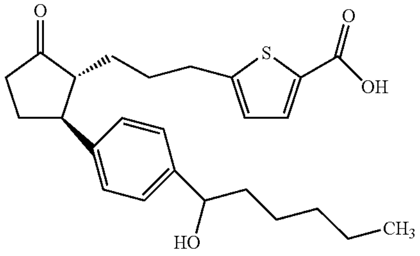 | 54 | | | NA | NA | 2 (3)[a] | 55 | >10 K | NA | NA | NA |
| 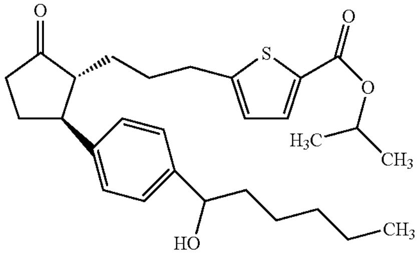 | | | | | | | | | | | |
| 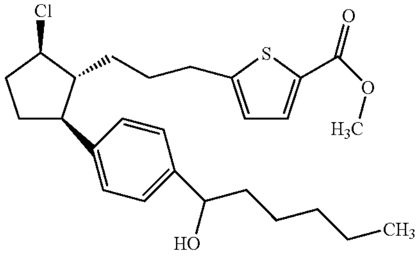 | | | | | | | | | | | |
| 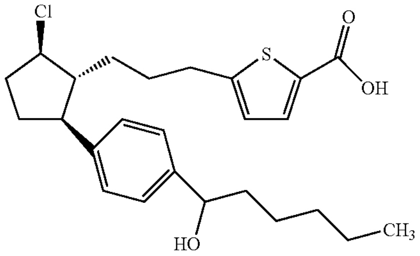 | | | | | | | | | | | |

TABLE 2
| STRUCTURE | BINDING HEP2 | FUNCTIONAL HEP2 |
|---|---|---|
| 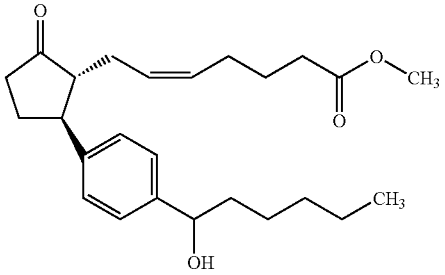 | 15000 | 15000 |
| 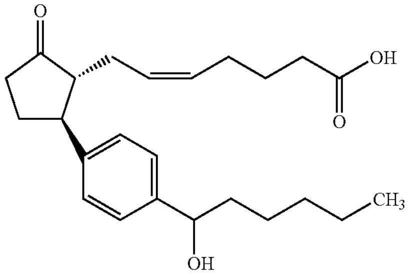 | 700 | 1011 |
| 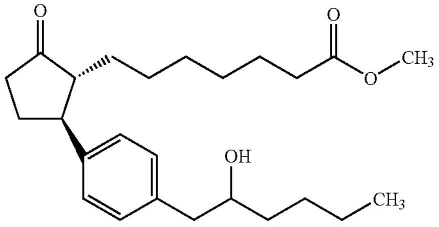 | 4600 | 15000 |
| 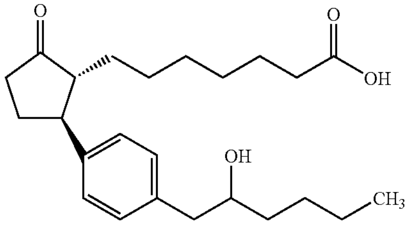 | 700 | 343 |
| 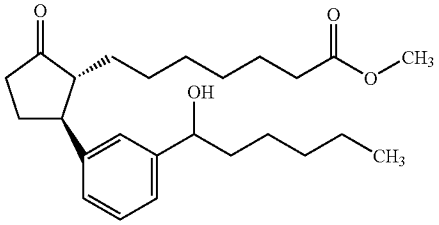 | 50000 | 50000 |
| 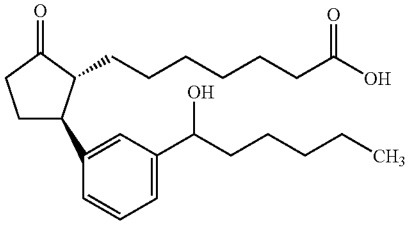 | 15000 | 50000 |

TABLE 2-continued
| STRUCTURE | BINDING HEP2 | FUNCTIONAL HEP2 |
|---|---|---|
| 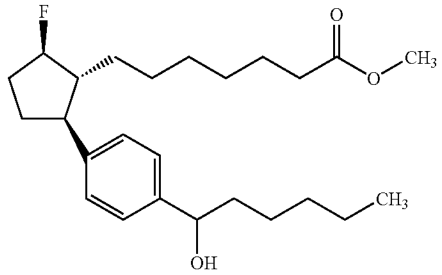 | 50000 | 50000 |
| 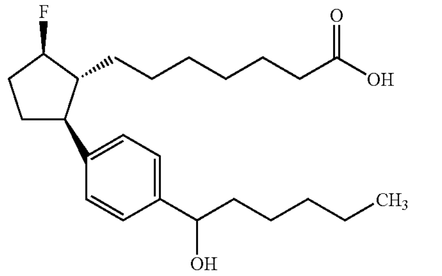 | 600 | 15000 |
| 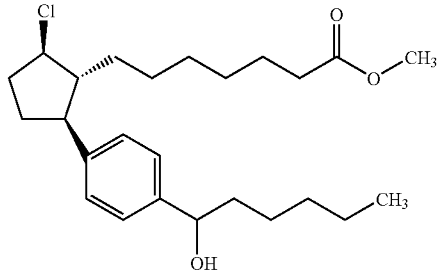 | 50000 | 50000 |
| 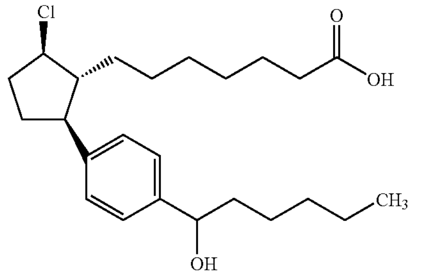 | 1900 | 15000 |
| 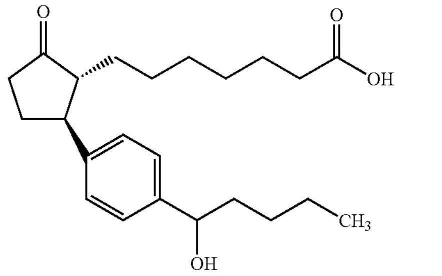 | 1400 | 1409 |

TABLE 2-continued
| STRUCTURE | BINDING HEP2 | FUNCTIONAL HEP2 |
|---|---|---|
| 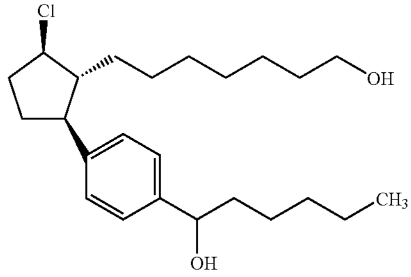 | 50000 | 50000 |
| 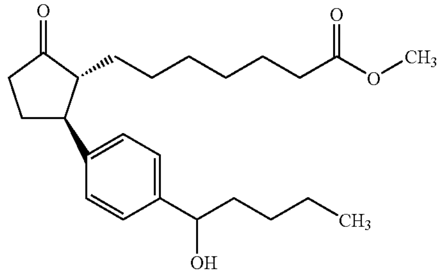 | 15000 | 15000 |
| 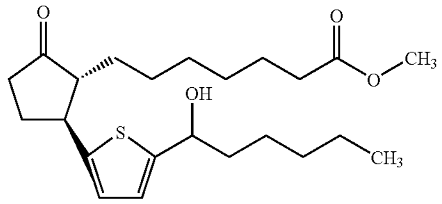 | 7100 | 7100 |
| 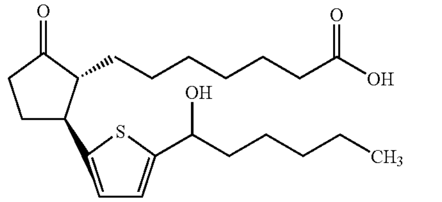 | 600 | 769 |
| 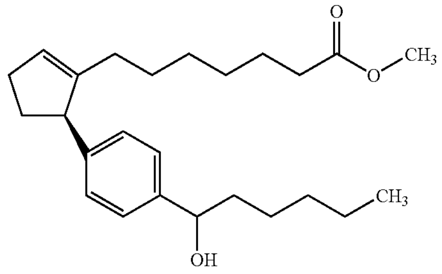 | 50000 | 50000 |

TABLE 2-continued
| STRUCTURE | BINDING HEP2 | FUNCTIONAL HEP2 |
|---|---|---|
| 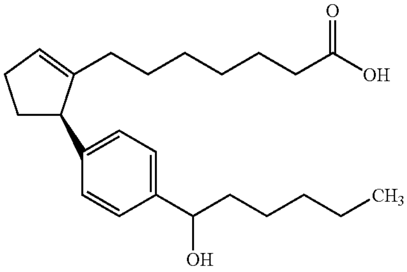 | 2811 | 4877 |
TABLE 3
| STRUCTURE | BINDING ($K_1$, nM) | | | FUNCTIONAL (Ca2+, EC50, nM) | | | | | | | |
|---|---|---|---|---|---|---|---|---|---|---|---|
| | HEP2 | HEP3 | HEP4 | HFP | HEP1 | HEP2 | HEP3A | HEP4 | HTP | HIP | HDP |
| 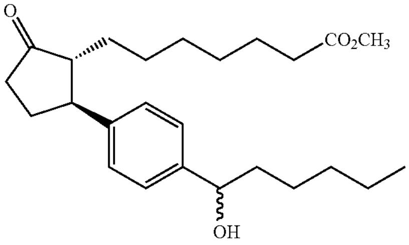 | 4677 | NA | 15000 | NA | NA | 2162 | 3090 | NA | NA | NA | NA |
| 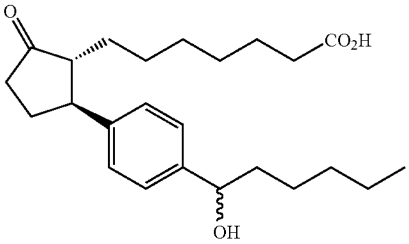 | 871 | 5200 | 15000 | NA | NA | 284 | 90 | NA | NA | NA | NA |
| 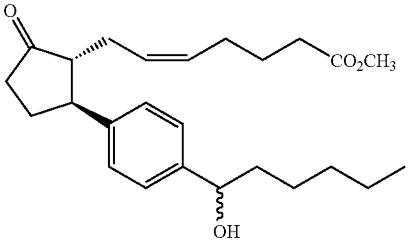 | 15000 | | 15000 | NA | NA | 15000 | 15000 | NA | NA | NA | NA |
| 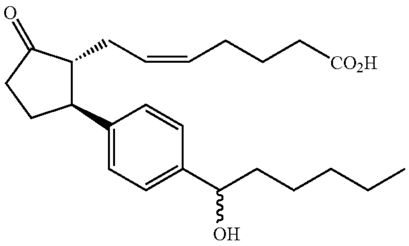 | 700 | 15000 | 15000 | NA | NA | 1011 | 552 | NA | NA | NA | NA |

TABLE 3-continued
| STRUCTURE | EP2 cAMP EC50 (nM) | EP2 Ki (nM) | EP2 Ca2+ EC50 (nM) | EP4 cAMP EC50 (nM) | EP4 Ki EC50 (nM) | EP4 Ca2+ EC50 (nM) | OTHER RECEPTORS Ca2+ EC50 (nM) |
|---|---|---|---|---|---|---|---|
| 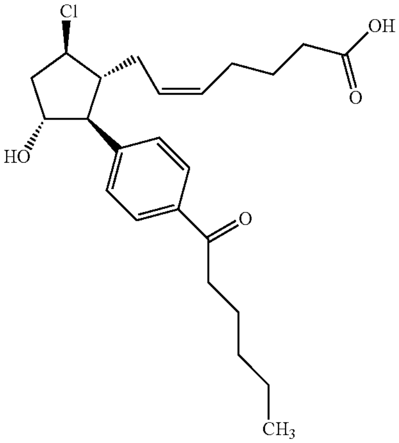 | 9 | 111 | 31 | | 2809 | NA | NA: EP1, EP3, DP, FP, IP, TP |
| STRUCTURE[a] | BINDING -Ki (nM) EP2 | BINDING -Ki (nM) EP4 | $Ca^{2+}$Signal-EC50 (nM)[b] FP | EP1 | EP2 | EP3 | EP4 | TP | IP | DP |
|---|---|---|---|---|---|---|---|---|---|---|
| 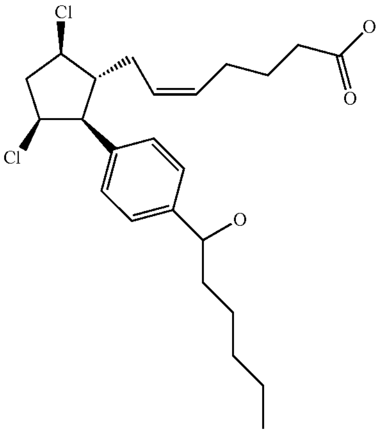 | 504 | 2364 | not active | not active | 427 (58) | 449 | 10,000 | not active | not active | not active |
| 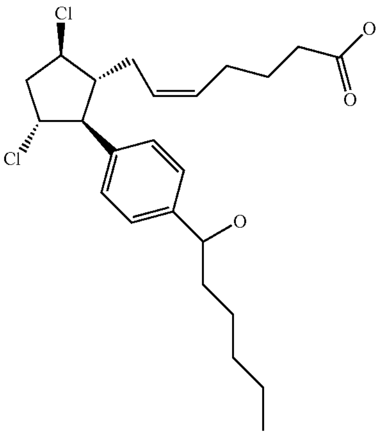 | 25 | 1400 | not active | not active | 15 (4) | 25 | not active | not active | not active | not active |

TABLE 3-continued

| | | | | | | | | | | |
|---|---|---|---|---|---|---|---|---|---|---|
| 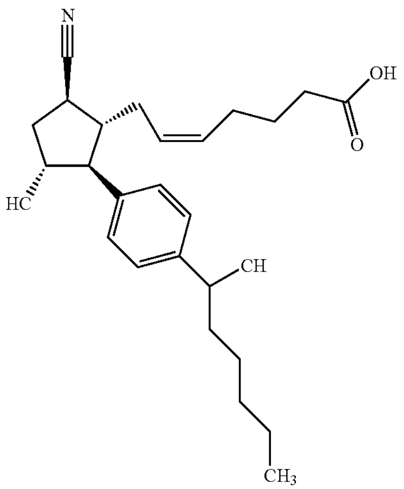 | 1252 | >10K | not active | not active | 34 (4) | 10000 | not active | not active | not active | not active |

(a) Refers to $EC_{50}$ in a cAMP mediated assay
NA means "not active."

In Vivo Testing

Intraocular Pressure (IOP)

Intraocular pressure studies in dogs involved pneumatonometry performed in conscious, Beagle dogs of both sexes (10-15 kg). The animals remained conscious throughout the study and were gently restrained by hand. Drugs were administered topically to one eye as a 25 μL volume drop, the other eye received 25 μL vehicle (0.1% polysorbate 80:10 mM TRIS) as a control. Proparacaine (0.1%) was used for corneal anesthesia during tonometry. Intraocular pressure was determined just before drug administration and at 2, 4 and 6 hr thereafter on each day of the 5 day study. Drug was administered immediately after the first IOP reading.

Ocular Surface Hyperemia

Ocular surface hyperemia was visually assessed and scored according to a system typically used clinically.

| Hyperemia Score | Assigned Value |
|---|---|
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range. Similar tests were used to determine ocular surface hyperemia on monkeys and rabbits. The Table below shows results of testing for certain compounds.

| | | DOG | | MONKEY | |
|---|---|---|---|---|---|
| STRUCTURE | Conc. (g/100 mL) | Max. ΔIOP (mm Hg) | Max. hyperemia | Max. ΔIOP (mm Hg) | RABBIT Max. hyperemia |
| 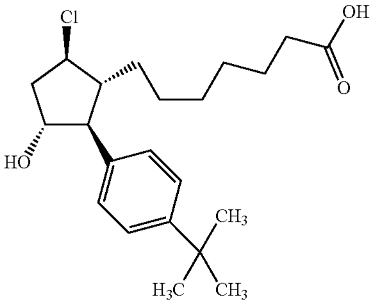 | 0.10% | −4 | 0.9 | | 0 |

-continued
| STRUCTURE | Conc. (g/100 mL) | DOG Max. ΔIOP (mm Hg) | DOG Max. hyperemia | MONKEY Max. ΔIOP (mm Hg) | RABBIT Max. hyperemia |
|---|---|---|---|---|---|
| 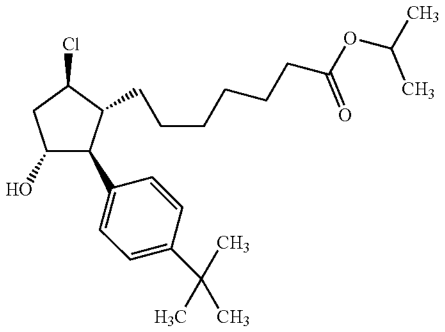 | 0.01% | | | 8 | 0.1 |
| 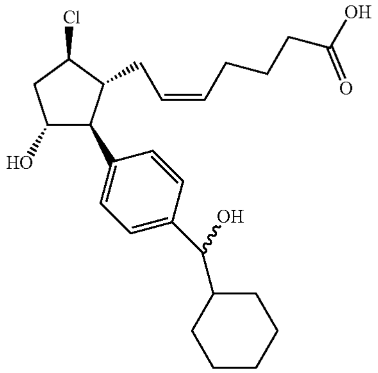 | 0.10% | −4 | 1 | | 0 |
| 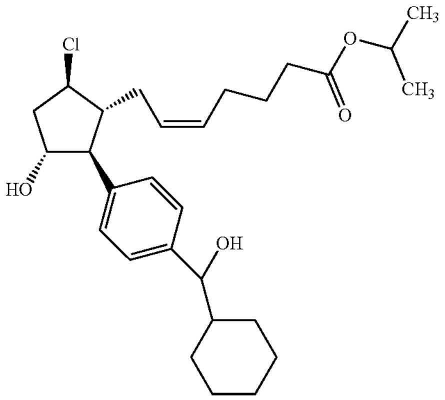 | 0.01% | −4 | 0.6 | 5 | |
| 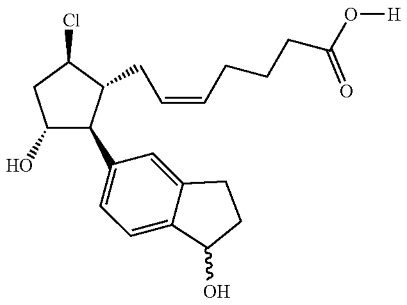 | 0.30% | −7 | 1 | 7 | |

-continued
| STRUCTURE | Conc. (g/100 mL) | DOG Max. ΔIOP (mm Hg) | DOG Max. hyperemia | MONKEY Max. ΔIOP (mm Hg) | RABBIT Max. hyperemia |
|---|---|---|---|---|---|
| 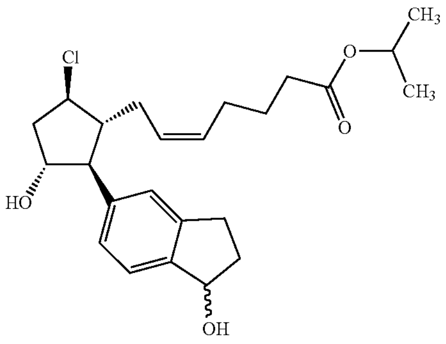 | 0.10% | −12 | | | 0.25 |
| 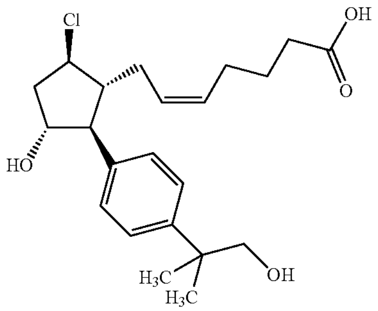 | 0.30% | −8 | 0.9 | | |
| 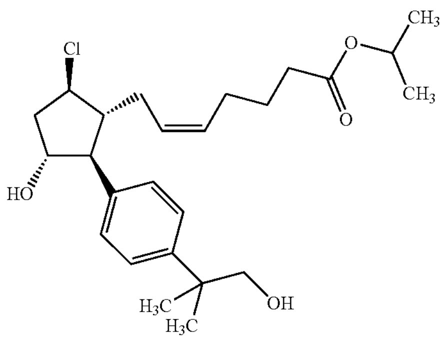 | 0.10% | −5 | 0.7 | 6 | 0.1 |
| 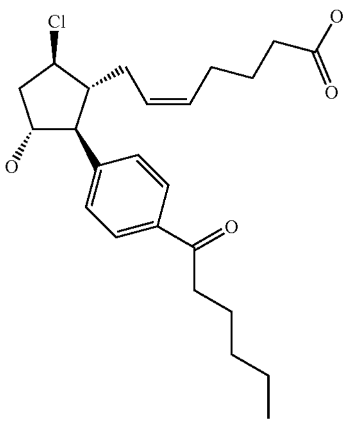 | 0.1% | −50 | 2.0 | 31 | |

-continued

| STRUCTURE | Conc. (g/100 mL) | DOG Max. ΔIOP (mm Hg) | DOG Max. hyperemia | MONKEY Max. ΔIOP (mm Hg) | RABBIT Max. hyperemia |
|---|---|---|---|---|---|
| 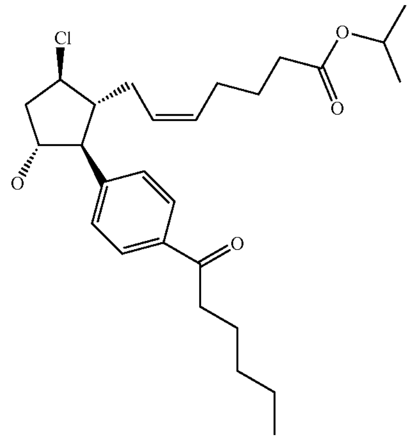 | 0.1% | −37 | 0.8 | 20 | 0 |
| 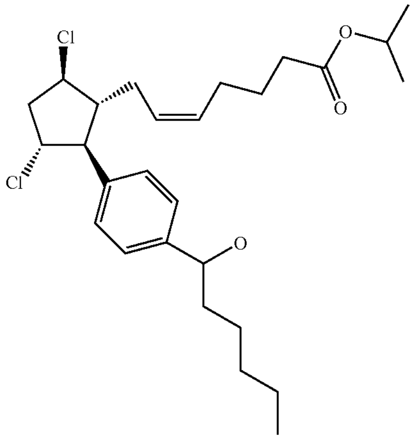 | 0.1% | −12 | 0.6 | 19 | 0.0 |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:

1. A compound having a formula

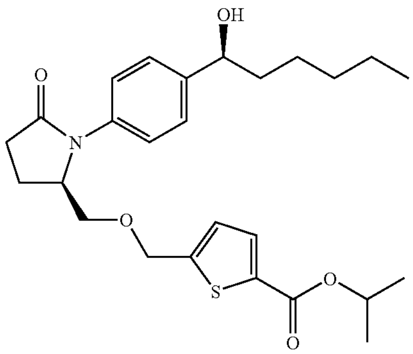

or a pharmaceutically acceptable salt or tautomer thereof;

wherein the compound has an $EC_{50}$ value of 20 nM or less in HEK-EBNA cells expressing a PG EP2 receptor subtype according to a cAMP assay.

2. The compound of claim 1, wherein the compound reduces intraocular pressure of a beagle dog having a mass of from about 10 to about 15 kg by at least 4 mmHg when administered topically in a liquid composition to an eye of said dog, wherein said composition has concentration of about 0.3% (w/v).

3. The compound of claim 2 wherein the mass of the beagle dog is about 10 kg.

4. The compound of claim 2 wherein the mass of the beagle dog is about 15 kg.

5. The compound of claim 2 wherein intraocular pressure is obtained by pneumatonometry.

6. The compound of claim 3 wherein intraocular pressure is obtained by pneumatonometry.

7. The compound of claim 5 wherein the compound reduces the intraocular pressure of the dog by at least 4 mmHg at one or more of about 2, about 4, or about 6 hours after a single administration.

8. The compound of claim 6 wherein the compound reduces the intraocular pressure of the dog by at least 4 mmHg at one or more of about 2, about 4, or about 6 hours after a single administration.

9. The compound of claim 8 wherein the compound reduces the intraocular pressure of the dog by at least 4 mmHg at about 2 hours after a single administration.

10. The compound of claim 8 wherein the compound reduces the intraocular pressure of the dog by at least 4 mmHg at about 4 hours after a single administration.

11. The compound of claim 8 wherein the compound reduces the intraocular pressure of the dog by at least 4 mmHg at about 6 hours after a single administration.

12. The compound of claim 8 wherein said liquid composition consists of the compound having a concentration of about 0.3% (w/v) or less, 0.1% (w/v) polysorbate 80, 10 mM TRIS, and water.

13. The compound of claim 9 wherein said liquid composition consists of the compound having a concentration of about 0.3% (w/v) or less, 0.1% (w/v) polysorbate 80, 10 mM TRIS, and water.

14. The compound of claim 2 wherein 0.1% (w/v) proparcaine is used for corneal anesthesia during pneumnatonometry.

15. The compound of claim 12 wherein 0.1% (w/v) proparcaine is used for corneal anesthesia during pneumatonometry.

16. The compound of claim 13 wherein 0.1% (w/v) proparcaine is used for corneal anesthesia during pneumatonometry.

17. The compound of claim 2 wherein the compound reduces the intraocular pressure of the dog by at least 4 mmHg at one or more of about 2, about 4, or about 6 hours after a single administration.

18. The compound of claim 2 wherein said liquid composition consists of the compound having a concentration of about 0.3% (w/v) or less, 0.1% (w/v) polysorbate 80, 10 mM TRIS, and water.

19. The compound of claim 1, wherein the compound reduces intraocular pressure of a human with glaucoma or elevated intraocular pressure by at least 5 mmHg when administered topically in a liquid composition to an eye of said human, wherein compound has a concentration of about 0.3% (w/v) or less in said composition.

* * * * *